(12) United States Patent
Hamel et al.

(10) Patent No.: US 6,982,063 B2
(45) Date of Patent: Jan. 3, 2006

(54) AUTOMATED PIPETTING SYSTEM

(75) Inventors: Marc F. Hamel, Hudson, NH (US); Greg Mathus, Concord, MA (US); Richard Cote, Sudbury, MA (US); Yoshio Maeda, Ibaraki (JP); Chikashi Ohtomo, Tokyo (JP)

(73) Assignees: Matrix Technologies Corp, Hudson, NH (US); Cosmotec Co., Ltd., Tokyo (JP)

( * ) Notice: Subject to any disclaimer, the term of this patent is extended or adjusted under 35 U.S.C. 154(b) by 581 days.

(21) Appl. No.: 09/865,404

(22) Filed: May 25, 2001

(65) Prior Publication Data

US 2002/0176803 A1 Nov. 28, 2002

(51) Int. Cl.
*B01L 3/02* (2006.01)
*G01N 1/10* (2006.01)
*G01N 21/00* (2006.01)

(52) U.S. Cl. .......................... 422/100; 422/63; 422/65; 436/180; 73/863.32; 73/864; 73/864.01; 73/864.11; 73/864.16; 73/864.25

(58) Field of Classification Search ................. 422/99, 422/100, 63, 64–67; 436/180; 73/863.32, 73/863.91, 864, 864.01, 864.11, 864.16, 864.17, 73/864.23, 864.31
See application file for complete search history.

(56) References Cited

U.S. PATENT DOCUMENTS

| | | |
|---|---|---|
| 3,708,264 A | 1/1973 | Jottier |
| 4,187,077 A | 2/1980 | Covington et al. |
| 4,824,642 A | 4/1989 | Lyman et al. |
| 4,830,832 A | 5/1989 | Arpagaus et al. |
| 5,057,281 A | 10/1991 | Torti et al. |
| 5,061,449 A | 10/1991 | Torti et al. |
| 5,061,639 A | 10/1991 | Lung et al. |

(Continued)

FOREIGN PATENT DOCUMENTS

EP 1070540 1/2001

(Continued)

OTHER PUBLICATIONS www.hudsoncontrol.com/products/tps.htm, 2000-2003.*

(Continued)

*Primary Examiner*—Jill Warden
*Assistant Examiner*—Brian R. Gordon
(74) *Attorney, Agent, or Firm*—Wolf, Greenfield & Sacks, P.C.

(57) ABSTRACT

A highly automated, high volume multichannel pipetting system which transfers liquid from mother plates to daughter plates, or from a fill station to daughter plates. The mother plates are stacked in one set of stacker assemblies, while the empty daughter plates are stacked in another stacker assembly. A plate handling assembly which is capable of moving the plates in three orthogonal directions retrieves the plates from the stacker assemblies, carries them to the pipetting head, and returns them to other stacker assemblies. The pipetting head is removable for replacement or repair thereof, or for insertion of another head assembly having a different number of pipetting channels. The head slides into the housing on slideways, and is retained in place by manually operable, threaded knobs mounted on shafts. The stacker assemblies include a chimney which is removable from a base. The plates may be stacked in the chimney and then inserted on the base. The base includes solenoids whose arms are retractable to permit plates to be retrieved or replaced one at a time. The chimneys contain flaps which serve to retain the plates within the chimney if manually removed from the base. Doors in the stacker chimneys allow manual insertion and replacement of plates. Methods of operation of the pipetting system are also disclosed.

17 Claims, 24 Drawing Sheets

U.S. PATENT DOCUMENTS

| | | | |
|---|---|---|---|
| 5,104,621 A | 4/1992 | Pfost et al. | |
| 5,415,060 A | 5/1995 | DeStefano, Jr. | |
| 5,653,942 A | 8/1997 | Terashima et al. | |
| 5,865,224 A | 2/1999 | Ally et al. | |
| 5,988,236 A | 11/1999 | Fawcett | |
| 6,148,878 A | 11/2000 | Ganz et al. | |
| 6,182,719 B1 | 2/2001 | Yahiro | |
| 6,255,116 B1 | 7/2001 | Leber et al. | |
| 6,258,324 B1 | 7/2001 | Yiu | |
| 6,299,840 B1 | 10/2001 | Watanabe et al. | |
| 6,358,470 B1 | 3/2002 | Higuchi | |
| 6,360,792 B1 | 3/2002 | Ganz et al. | |
| 6,372,185 B1 | 4/2002 | Shumate et al. | |
| 6,395,231 B1 | 5/2002 | Kraemer et al. | |
| 6,399,024 B1 | 6/2002 | Bevirt et al. | |
| 6,436,351 B1 * | 8/2002 | Gubernator et al. | 422/102 |
| 6,464,943 B1 * | 10/2002 | Yiu | 422/100 |
| 6,589,483 B1 * | 7/2003 | Maeda | 422/100 |
| 2001/0005489 A1 | 6/2001 | Roach et al. | |
| 2001/0039843 A1 | 11/2001 | Schoeppe | |
| 2002/0104389 A1 | 8/2002 | Hovey | |
| 2003/0027345 A1 * | 2/2003 | Friswell et al. | 436/49 |

FOREIGN PATENT DOCUMENTS

JP (A)H07-244052 9/1995

OTHER PUBLICATIONS

Micro-Volume Pipetting, PerkinElmer, 2000.*
www.tomtec.com/Pages/Quadra3.html.*
www.microwells.com/pp-55550MS_detail.htm.*
www.beckman.com/products/instrument/automatedsolutions/multimek.*
www.robotec.co.uk/personal_pipettors.html.*
http://las.perkinelmer.com/catalog/Product.aspx?ProductID=MiniTrak.*
http://las.perkinelmer.com/catalog/Apricot Personal Pipettor Family.*
http://bekman-coulter.com/products/introument/Biomek NX Laboratory Automation Workstation.*
www.tomen.com Quadra 3.*
"Tango Liquid Handling System" brochure, Robbins Scientific Corporation, 2000.
"384/96 Well Automatic Pipettor" brochure, Labcyte, Dec. 2000.
"EDR384S/96S Pipetting Workstation" brochure, Labcyte, Dec. 2000.
CCS Packard PlateStak® brochure.
"Apricot Designs" brochure, PerkinElmer Life Sciences, 2000.
"CyBi-Screen-machine, One system-Many Solutions" brochure, CyBio, Inc., Nov. 2000.
"JOBI-Well Systems & Accessories" brochure, updated Nov. 1998, Jenoptik Bioinstruments GmbH.
Index and product pages printed from www.tomtec.com, Tomtec, Jan. 26, 2001.
CCS Packard MultiPosition Dispense Module Automated 96- and 384-channel Pipettor brochure, 2000.
CCS Packard "Platetrak™ Creative Solutions for Automated Microplate Processing" brochure, 1998.

* cited by examiner

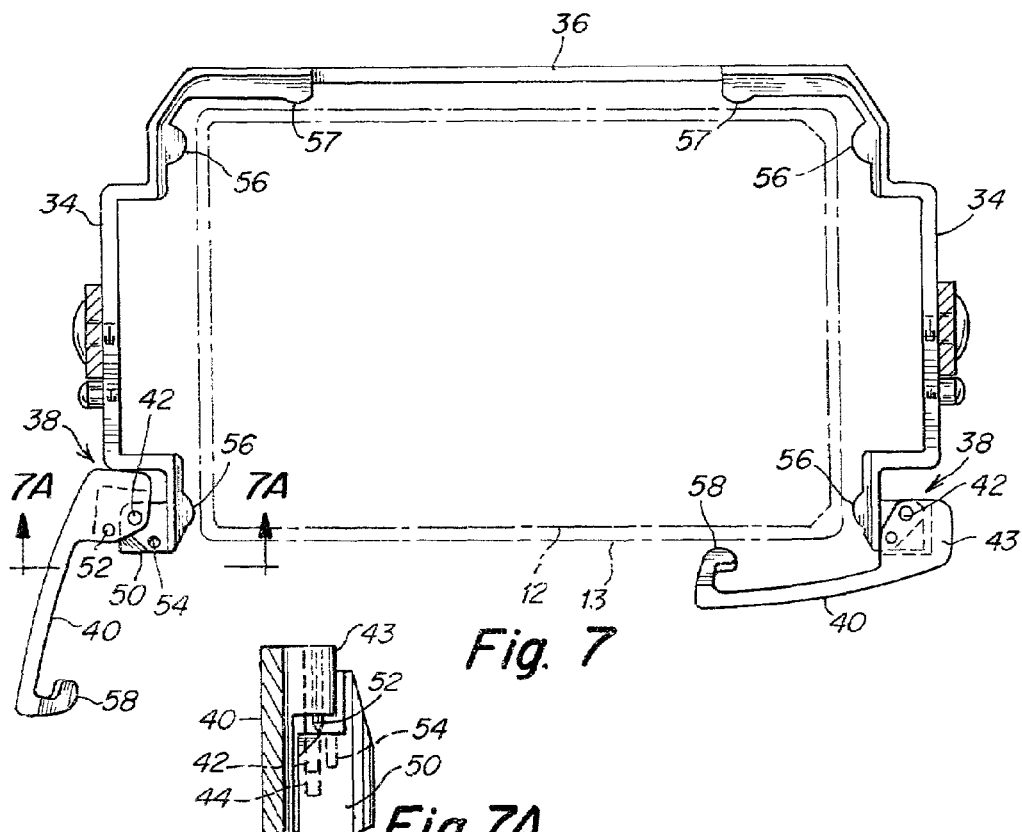
Fig. 7
Fig. 7A
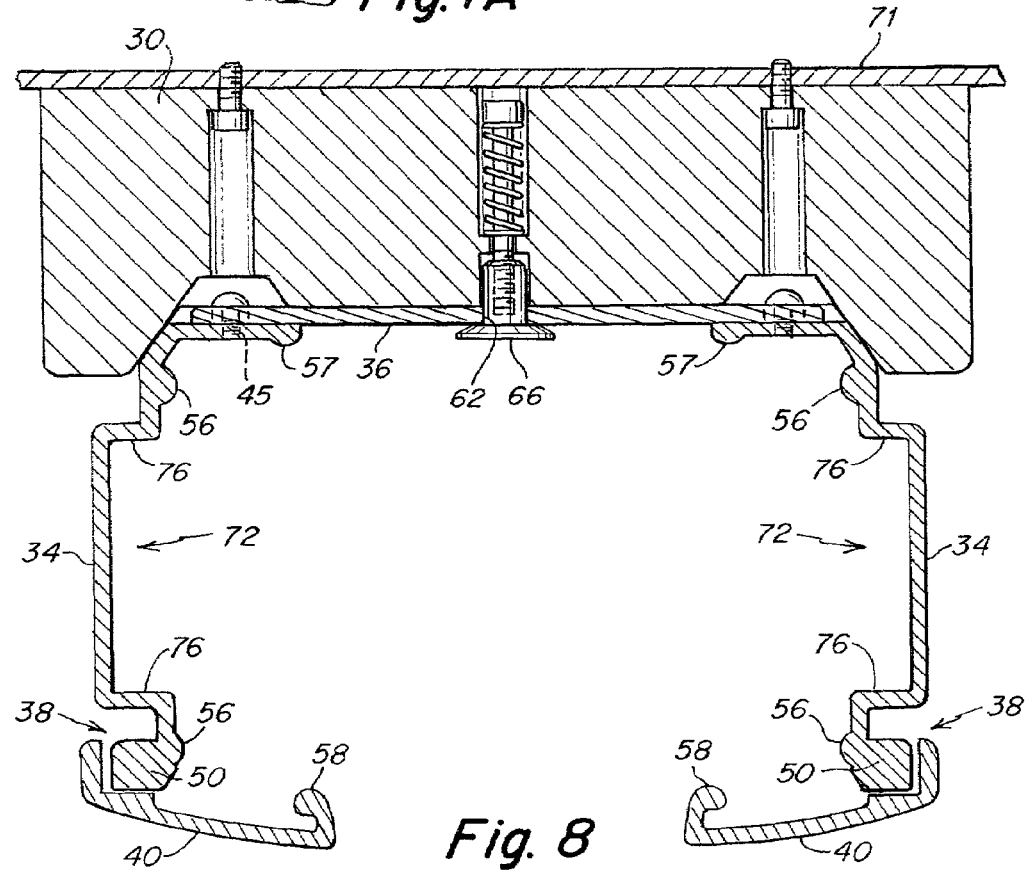
Fig. 8

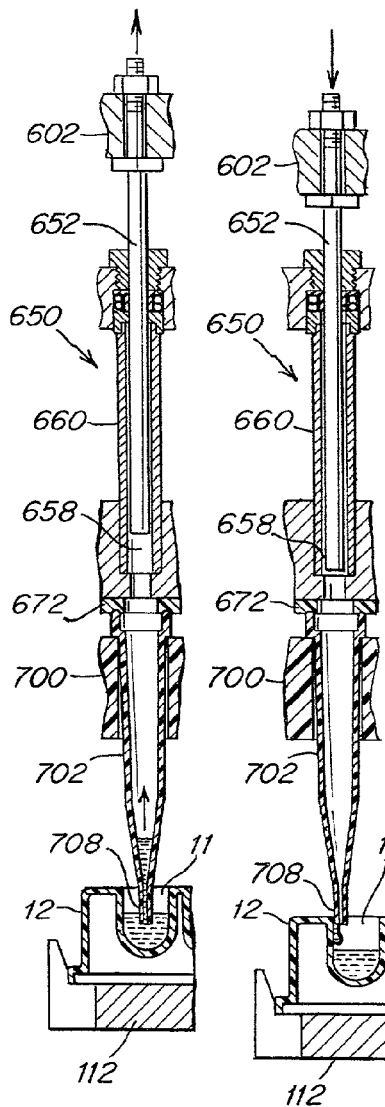
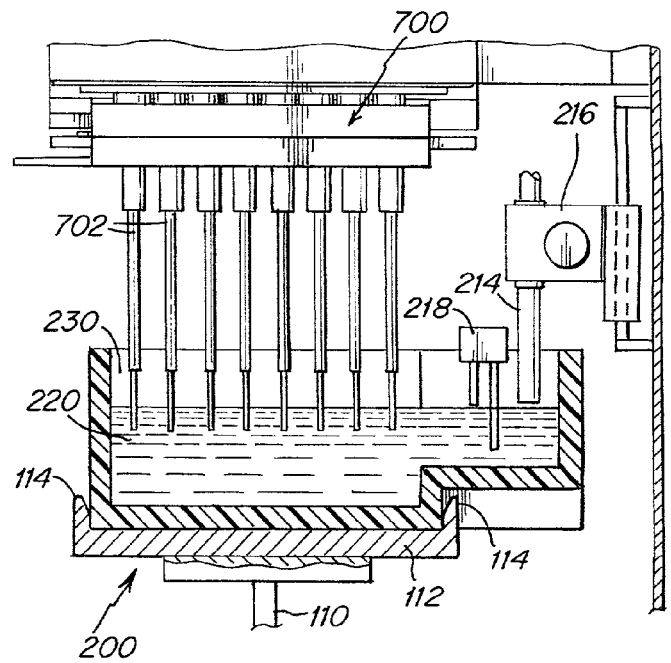
Fig. 23
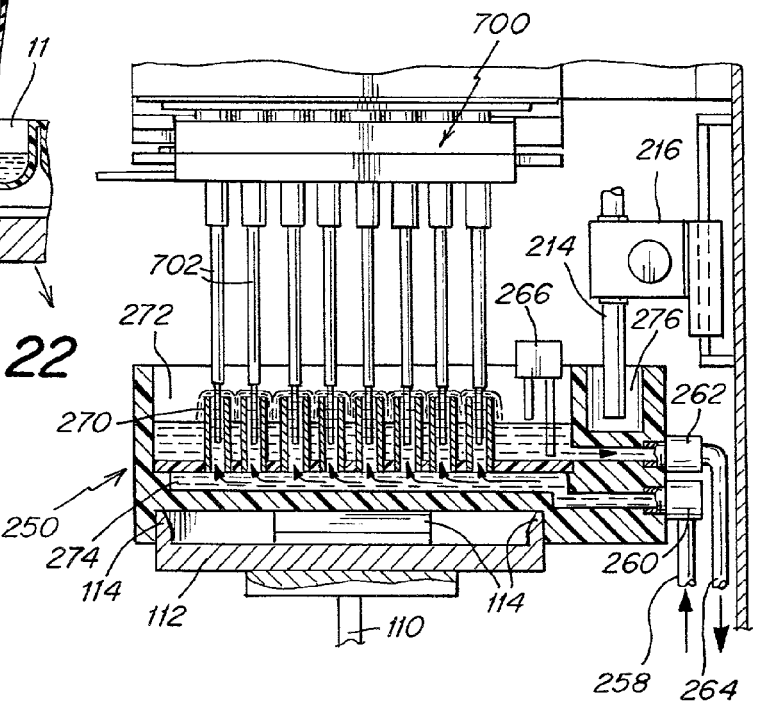
Fig. 21  Fig. 22
Fig. 24

AUTOMATED PIPETTING SYSTEM

FIELD OF THE INVENTION

This invention relates generally to liquid transfer and dispensing devices for liquid reagents and samples, and more particularly to a highly automated, high throughput multichannel pipetting system.

BACKGROUND OF THE INVENTION

Pipetting systems are well known, and typically are used in laboratories and hospitals for the aspiration and dispensing of relatively small, predetermined quantities of liquids into the wells of plates such as microplates or deep well blocks or the like. Examples of the liquids being dispensed include blood, other biological samples, solvents, reagents and the like. Liquid is normally drawn by suction from one set of plates or the like and subsequently released into the wells of other plates or the like. Typically, pipette tips are used to draw some or all of the fluid from one set of wells in a plate or reservoir and transfer it to another set of wells in another plate.

For high volume, automated systems, the spacing of the wells in one set of plates is the same as the spacing of the wells in the plates to which the fluid is being transferred. However, not all plates have the same well spacings, and not all plates have the same number of wells. Therefore, it is desirable to be able to vary the number of pipette tips, or the spacing between tips in such automated systems. Such flexibility is essential in most laboratories and hospitals. It is also desirable to be able to perform such operations rapidly and to be able to perform a high volume of operations in a very short period of time.

Many preexisting, automated, high volume systems are available and include those shown in U.S. Pat. Nos. 4,830,832, 6,148,878 and 5,988,236. Examples of hand held, non-automated pipetters are disclosed in U.S. Pat. Nos. 5,061,449, 4,824,642, 5,057,281, and 5,104,621.

Another known high throughput, automated pipetter was sold by Matrix Technologies, Inc. and Jenoptik Bioinstruments GmbH (now known as Cybio AG) of Jena, Germany under the trademarks JOBI-WELL and CYBI-WELL. In this system, liquid in so-called "mother plates" is transferred to other plates which are called "daughter plates." The mother plates are stacked vertically on one side of a stacking mechanism and are removed sequentially and transported to a pipetting head which removes liquid from the mother plates. These mother plates are then returned to a different side of the same stacking mechanism. Empty daughter plates are retrieved from one part of a stacking mechanism for the daughter plates and are transported to the pipetting head. The plate is then lifted up to the pipetting head for the dispensing of liquid previously retrieved from the mother plates. These filled daughter plates are then returned to a different part of the daughter plate stacking mechanism. These systems include features such as ink jet printers, bar code readers, different pipetting head configurations for different sized tips, different numbers of tips with different spacings, stacking mechanisms for both shallow well and deep well plates and tip wash stations.

Other automated systems are sold by Tomtec, 1000 Sherman Avenue, Hamden, Conn. 06451 and by Cosmotec Ltd. of Tokyo, Japan in which the pipetter utilizes stackers for the microplates. Both products are capable of handling microplates having different numbers of wells or different spacings between the wells.

SUMMARY OF THE INVENTION

The present invention relates to a multi-channel pipetting system that provides greater flexibility and higher throughput than prior art devices.

In one aspect, the invention includes a system having multiple stacker assemblies for supplying mother plates filled with a liquid to be dispensed, and empty daughter plates for receiving the liquid to be dispensed. A pipetting head assembly transfers liquid from the mother plates, or from a supply station, to daughter plates. In one embodiment of the invention, a plate handling assembly is provided which is moveable in three orthogonal directions to transfer plates from selected ones of the stacker assemblies to the pipetting head assembly for withdrawal of a liquid from mother plates, and for returning the mother plates to another stacker assembly. In another embodiment, the plate handling assembly moves daughter plates from a stacker assembly containing a supply of empty daughter plates, and transfers the daughter plates to the pipetting head assembly where the daughter plates are filled with liquid. Thereafter, the plate handling assembly returns the daughter plates to another stacker assembly. In each instance, the mother or daughter plate is supported by a pad which is capable of moving in three orthogonal directions to perform the desired task.

In another aspect of the invention, the pipetting head assembly is removable from its housing, to permit replacement with differently formatted heads having different volume capacity and number of channels, or repair. Preferably, the assembly slides in and out of the housing on slideways. A manually operable latching mechanism is provided to secure the pipetting head assembly to the housing. In one embodiment, the latching mechanism includes a plurality of threaded shafts which are pivotally mounted on the head and which include threaded knobs which are manually operated for securing of the head and removal thereof.

In yet another aspect of the invention, a tray containing the pipetting tips is separately removable from the head to permit replacement of the tips, or use of trays with different configurations as required. In one embodiment, the tray with the tips is clamped in place by spring biased brackets. In another embodiment, the upper ends of the tips are aligned with and surround openings in respective piston chambers of the pipetting head assembly, and a seal is effected around the wall of the upper end of the tip using a silicone pad or the like.

In yet another further aspect of the invention, each stacker assembly includes a base assembly and a removable chimney. The base assembly includes solenoids with retractable arms which support stacked plates within the assembly. The plates may be removed by retraction of the arms in conjunction with operation of the plate handling assembly.

In yet another further aspect, the chimneys include lower flaps which are biased into an open position for engaging plates to support the plates within the chimney when the chimney is removed from the base assembly and carried to another location. In one embodiment of this aspect, as the chimneys are placed in the base assembly, upstanding walls in the base assembly pivot the flaps into a closed position in which the plates are only supported by the solenoids so that the flaps do not interfere with the dispensing of plates from the assembly utilizing the solenoids.

In another embodiment, each chimney includes doors which may be opened for insertion of plates, but which can be locked in place when closed to prevent plates from inadvertently falling out. In a preferred embodiment, the locking mechanism includes a pin which seats in a hole and which can be raised out of the hole by raising of the door. The chimneys typically are provided with handles to allow manual carrying thereof. In addition, slots are provided on the back side of the chimneys for mating with buttons disposed on the housing to facilitate alignment of the chimneys with the base assemblies, as well as attachment of the chimneys to the base assembly. Preferably, there is a slot formed between the doors of the chimney when they are closed to allow manual insertion and removal of the plates from the top of the chimney. This slot preferably extends into the base.

In other aspects of the invention, a fill station for providing a supply of liquid to be dispensed to the daughter plates, and a wash station for washing pipette tips while in the head assembly may also be provided.

In another embodiment of the invention, a method of transferring liquid is disclosed in which plates are manipulated by an apparatus capable of moving in three orthogonal directions to transfer plates from a source of plates to a pipetting head and for returning plates to another location. Another aspect of the method includes the steps of stacking the plates within a stacker, retaining the plates within the stacker using retractable arms, withdrawing the arms to allow a single plate to pass through an opening and returning the arms to their extended position after dispensing of a plate.

BRIEF DESCRIPTION OF THE DRAWINGS

The objects, advantages and features of this invention will be more clearly appreciated from the following detailed description, when taken in conjunction with the accompanying drawings, in which:

FIG. 7 is a cross-sectional plan view of the stacker assembly of this invention taken along the line 7—7 of FIG. 6;

FIG. 7A is a fragmentary, detail view of a door latch as seen along the line 7A—7A of FIG. 7;

FIG. 8 is a cross-sectional plan view of the stacker assembly of this invention taken along the line 8—8 of FIG. 6;

FIG. 21 is a fragmentary detail view of a portion of FIG. 20 showing one piston of the head assembly of FIG. 16 removing liquid from a well;

FIG. 22 is a fragmentary detail view of a portion of FIG. 20 showing the piston of FIG. 21 dispensing liquid into a well;

FIG. 23 is a schematic, cross-sectional side view of the head assembly of FIG. 16 in conjunction with a fill station;

FIG. 24 is a schematic, cross-sectional side view of the head assembly of FIG. 16 in conjunction with a wash station;

DETAILED DESCRIPTION

Figure 1:
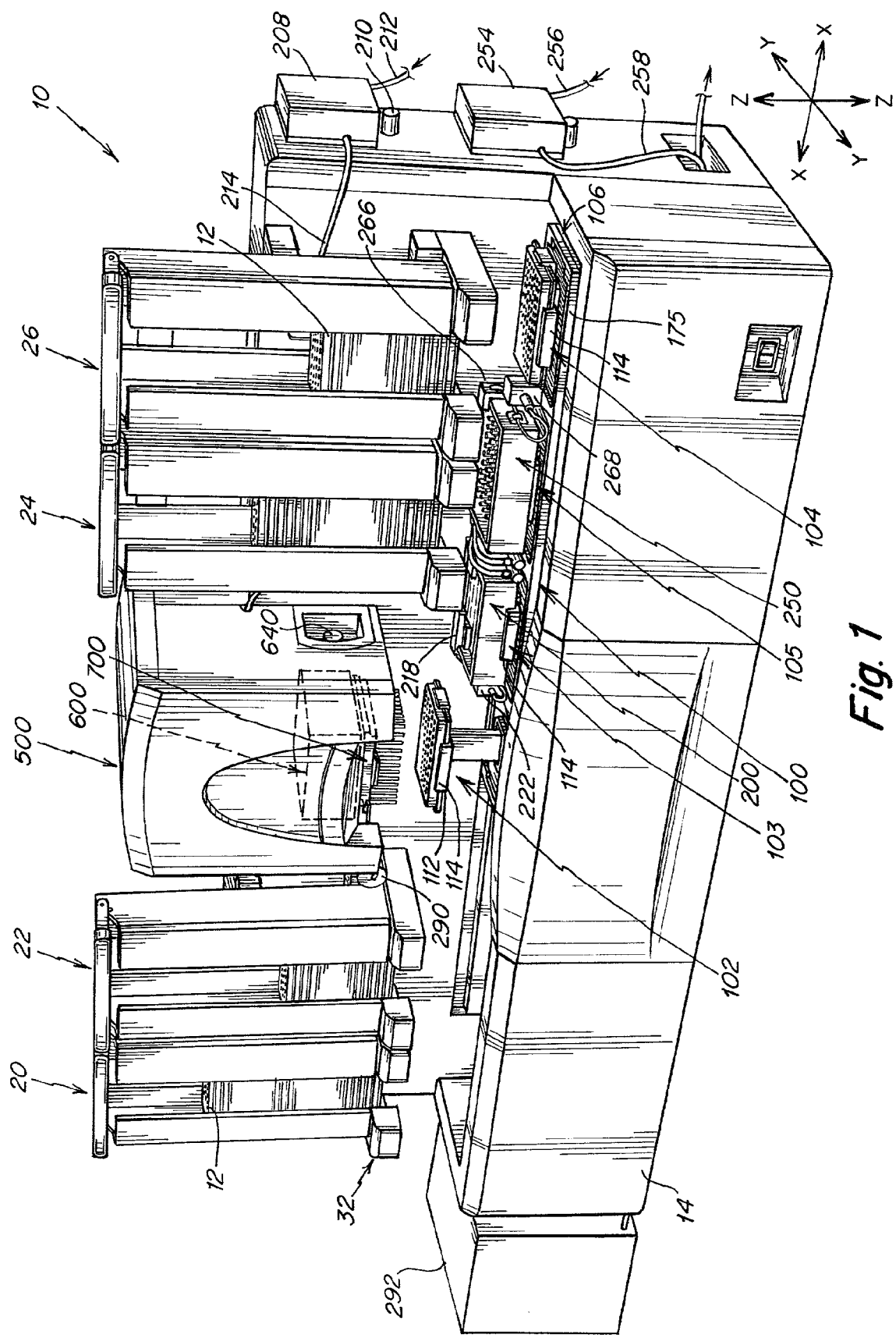
FIG. 1 is a front perspective view of the automated pipetting system of this invention.
Figure 2:
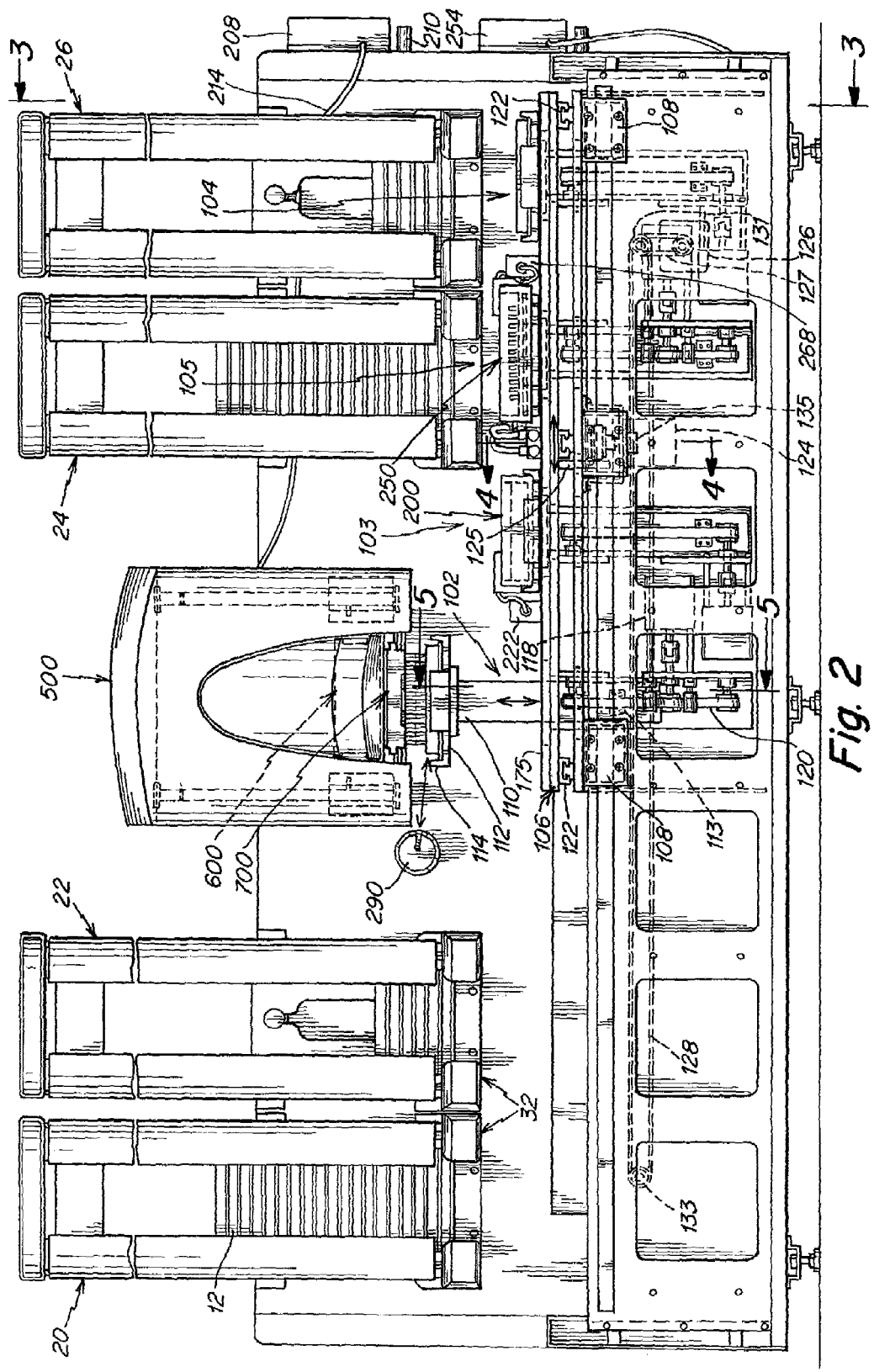
FIG. 2 is a front, elevational view of the pipetting system of FIG. 1 with the lower housing removed.

With reference now to the drawings, and more particularly to FIGS. 1 and 2 thereof, the automated pipetting system 10 of this invention will be described. Pipetting system 10 preferably includes stacker assemblies 20, 22, 24 and 26, pipetting head assembly 500 and plate handling assembly 100. Typically, system 10 includes a plurality of stacker assemblies and a pipetting head assembly 500, that includes at least one head 600, and stacker assemblies typically are disposed on either side of the pipetting head assembly 500. The plate handling assembly 100 transfers plates 12 between the pipetting head assembly 500 and various ones of the stacker assemblies 20–26 as will be described. The pipetting head assembly 500 withdraws liquid from certain "mother" plates 12 or a fill station 200 and transfers it to other "daughter" plates 12, as will be more fully described hereinafter. The operation of all components is controlled by a personal computer or programmable processor 292.

Plate handling assembly 100 will now be discussed with particular reference to FIGS. 1–5. Plate handling assembly 100 includes a carriage 106, and a plurality of plate lifters 102, 103, 104 and 105. Each of plate lifters 102, 103, 104 and 105 is substantially identical. In the discussion that follows, only a single plate lifter, plate lifter 102, will be discussed specifically. However, it is to be understood, that each of the other plate lifters 103, 104 and 105 is substantially identical to plate lifter 102 and has similar components and operates in a similar manner. In the particular configuration illustrated in FIGS. 1 and 2, first plate lifter 102 and second plate lifter 104 are used only to transfer plates 12, while plate lifters 103 and 105 are utilized to support and move fill station 200 and wash station 250 respectively. However, it is to be understood that plate lifters 103 and 105 could also be utilized to manipulate or move plates 12, or that fill station 200 and wash station 250 could be placed on platelifters 102 and 104.

Figure 16:
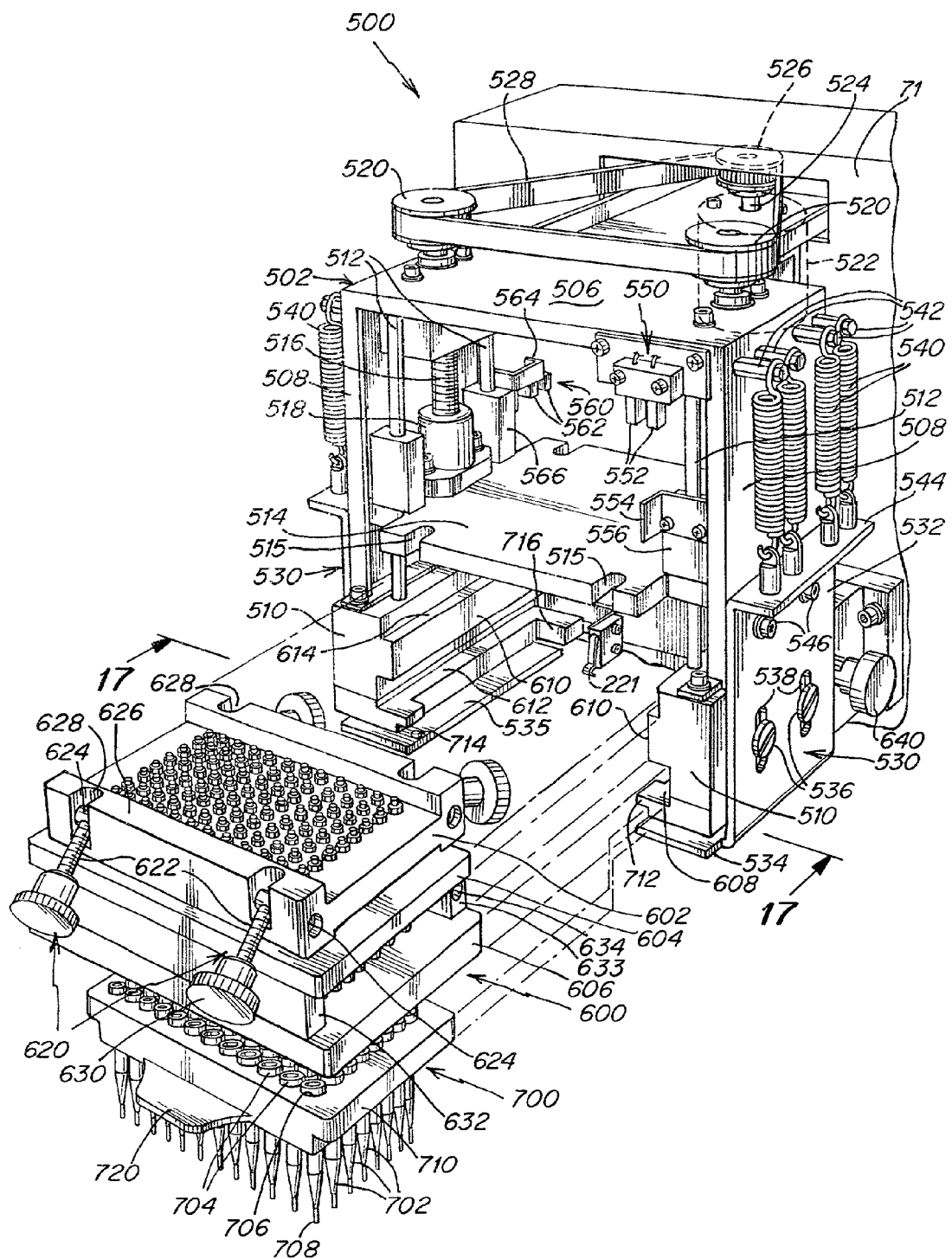
FIG. 16 is an exploded, front perspective view of the head assembly of this invention.
Figure 20:
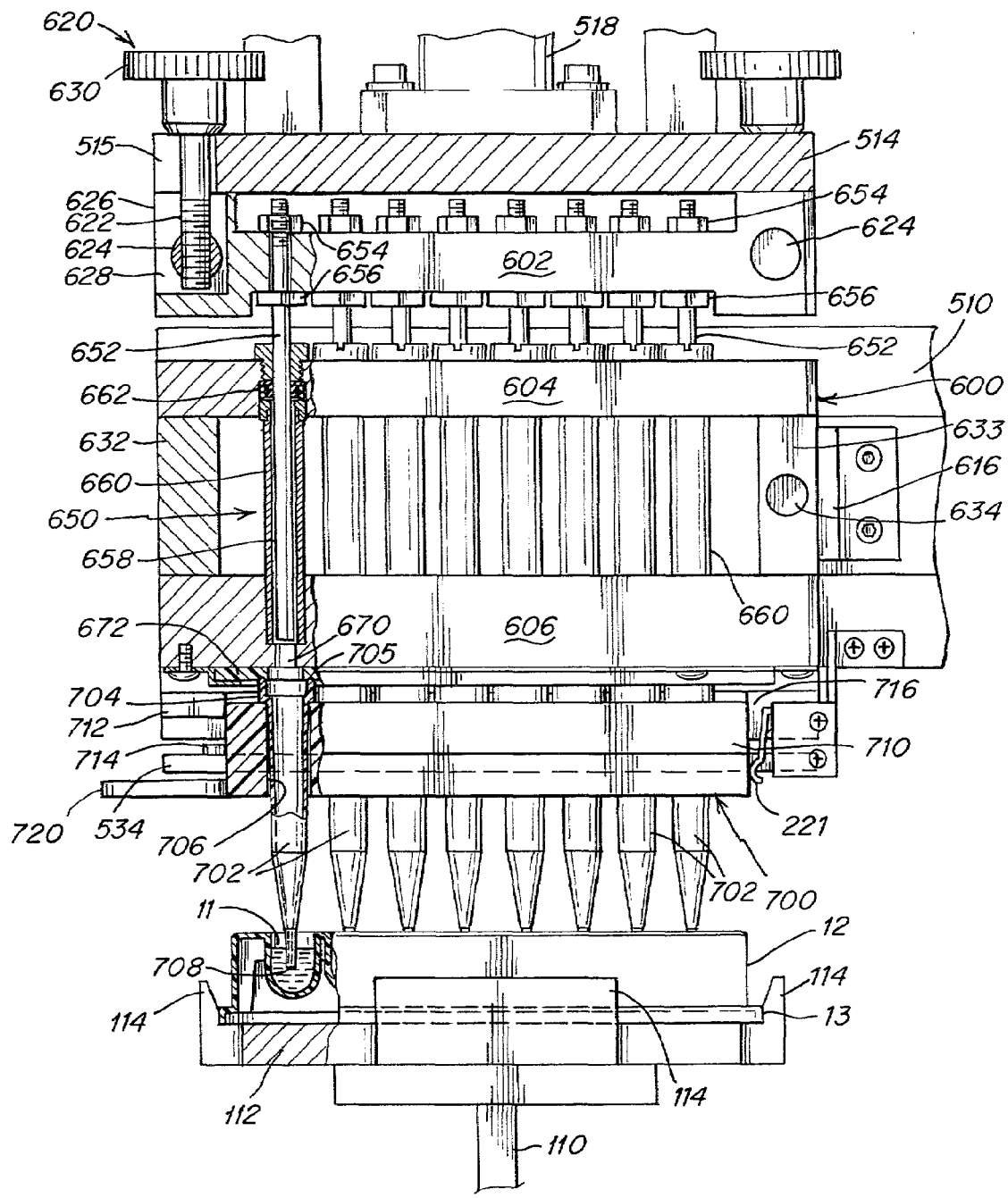
FIG. 20 is a fragmentary, cross-sectional detail side view taken along the line 20—20 of FIG. 17.

Plate lifters 102, 103, 104 and 105 all extend from carriage 106 and move in an X direction (as shown in FIG. 1) along with a carriage 106. Carriage 106 rides along X slides 108 in the X direction under the control of an X drive motor 126 and along Y slides 122 in the Y-direction under the control of a Y drive motor 124, to position plate lifters 102, 103, 104 and 105 at the desired location in the X and Y directions. Plate lifters 102, 103, 104 and 105 also move in the Z direction, as shown in FIG. 1, with respect to carriage 106, under the control of associated Z drive motors 118. In the configuration illustrated in FIGS. 1 and 2, plate lifters 102 and 104 are moved in the Z direction to retrieve and return plates 12 to the stacker assemblies 20–26, and to lift plates 12 up to head assembly 500. In the configuration illustrated in FIGS. 1 and 2, platelifter 103 is moved in the Z direction to raise the fill station to head assembly 500, as will be described, while plate lifter 105 is moved in the Z direction to raise wash station 250 to head assembly 500, as will be described. Movement in the Y direction allows adjustment of the position of plate lifters 102, 103,104 and 105 with respect to stacker assemblies 20–26 and head assembly 500, and allows use of plate lifters 102 and 104 to separate plates 12 that are stuck together in stacker assemblies 20–26, as will be described. X and Y movement of the platelifters also allows system 10 to be programmed to cause head 600 to withdraw liquid from a plate which has a substantially larger number of wells than assembly 500 has tips 702, and to expel liquid into daughter plates that also have a substantially larger number of wells than assembly 500 has tips 702 (FIG. 16). By moving plates 12 with respect to head 600, liquid may be withdrawn from or expelled into different quadrants of a substantially larger plate 12. Finally, movement in the X and Y directions permits movement of plates 12 with respect to the tips 702 of assembly 500 to provide access to different locations within a well 11, and to wipe liquid from the tips 702 on the edge of a well 11 (FIG. 20). Substantially all of the X, Y and Z drive motors and drive belts are preferably enclosed within a housing 14 for safety and aesthetic purposes.

Each plate lifter 102, 103, 104 and 105 preferably includes a column 110 having a pad 112 disposed on an upper end thereof. Pad 112 is sized to accept a plate 12, fill station 200 or a wash station 250 and optionally includes raised side walls 114 extending upwardly from pad 112 which prevent a plate 12, fill station 200 or wash station 250 from sliding off pad 112 in the X or Y directions.

Figure 3:
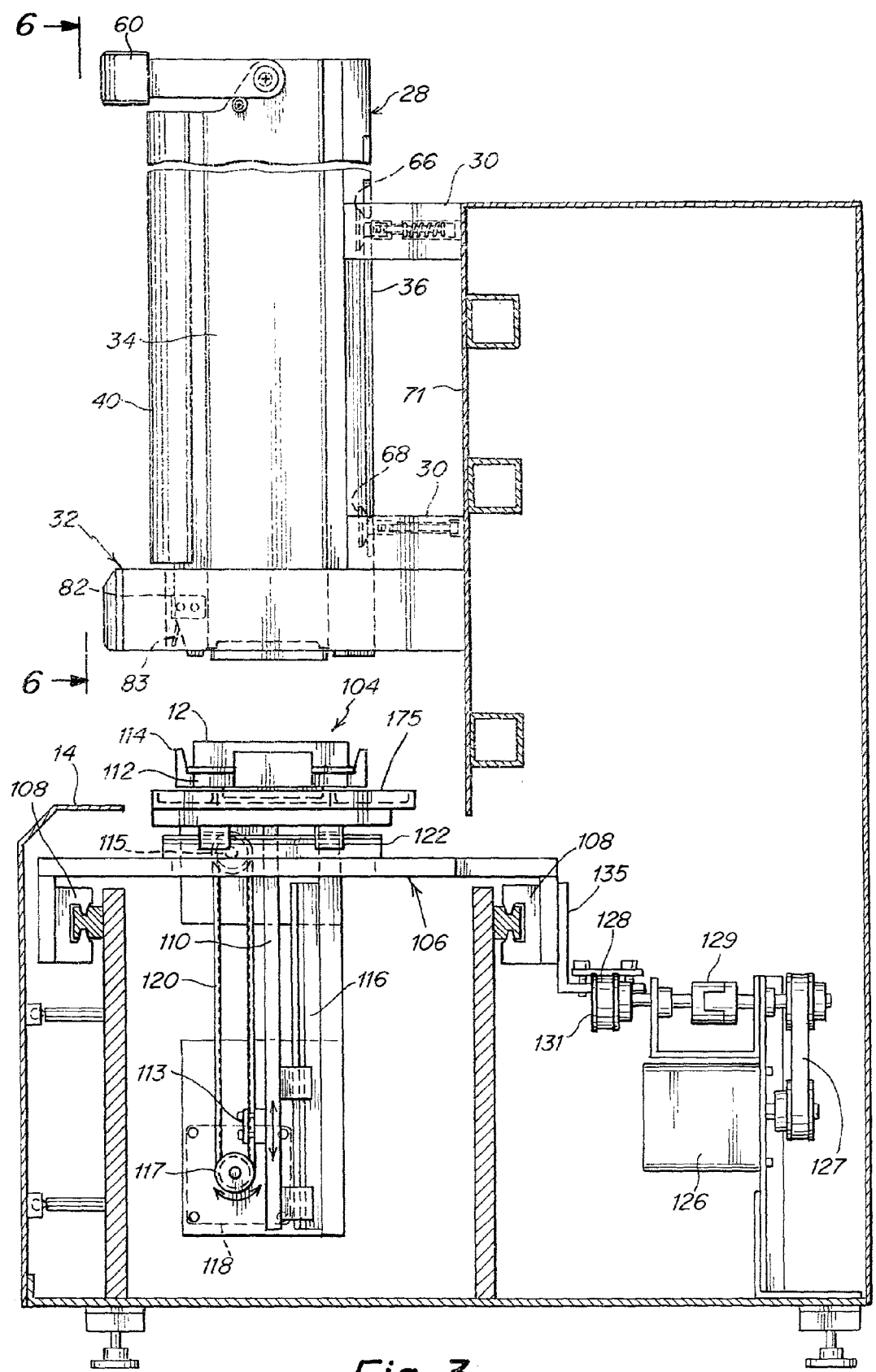
FIG. 3 is a cross-sectional, side view of the pipetting system of FIG. 2 taken along the line 3—3 of FIG. 2.

Details of one embodiment of the coupling between X drive motor 126 and carriage 106 is shown in FIG. 3. In this embodiment, X drive motor 126 is coupled by belt 127 to a flexible coupling 129 which is coupled in turn to a pulley 131 about which X drive belt 128 passes. X drive belt 128 extends substantially the entire length of housing 14 in the X direction and passes over an idler pulley 133 disposed at an opposite end of housing 14 from pulley 131. Belt 128 is coupled to carriage 106 by a bracket 135. It is understood, of course, that other conventional couplings and drive systems may be used to control movement of carriage 106 in the X direction.

Figure 5:
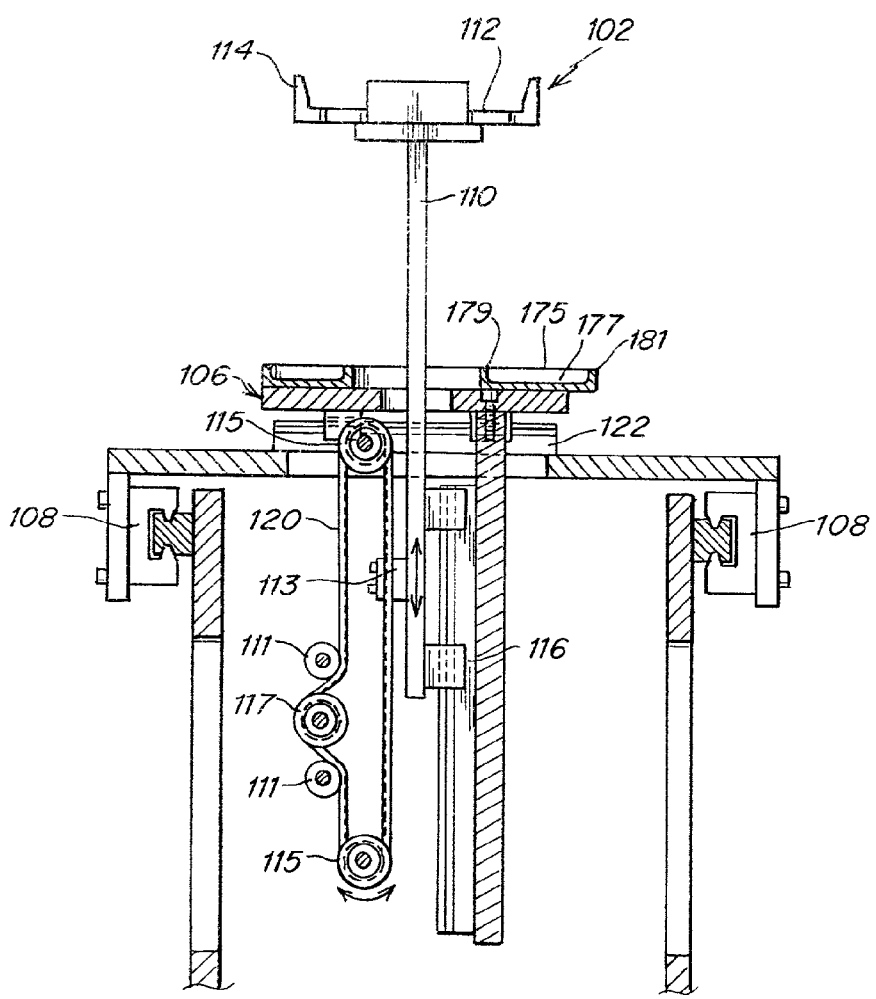
FIG. 5 is a fragmentary cross-sectional side view of the pipetting system of this invention taken along the line 5—5 of FIG. 2.
Figure 6:
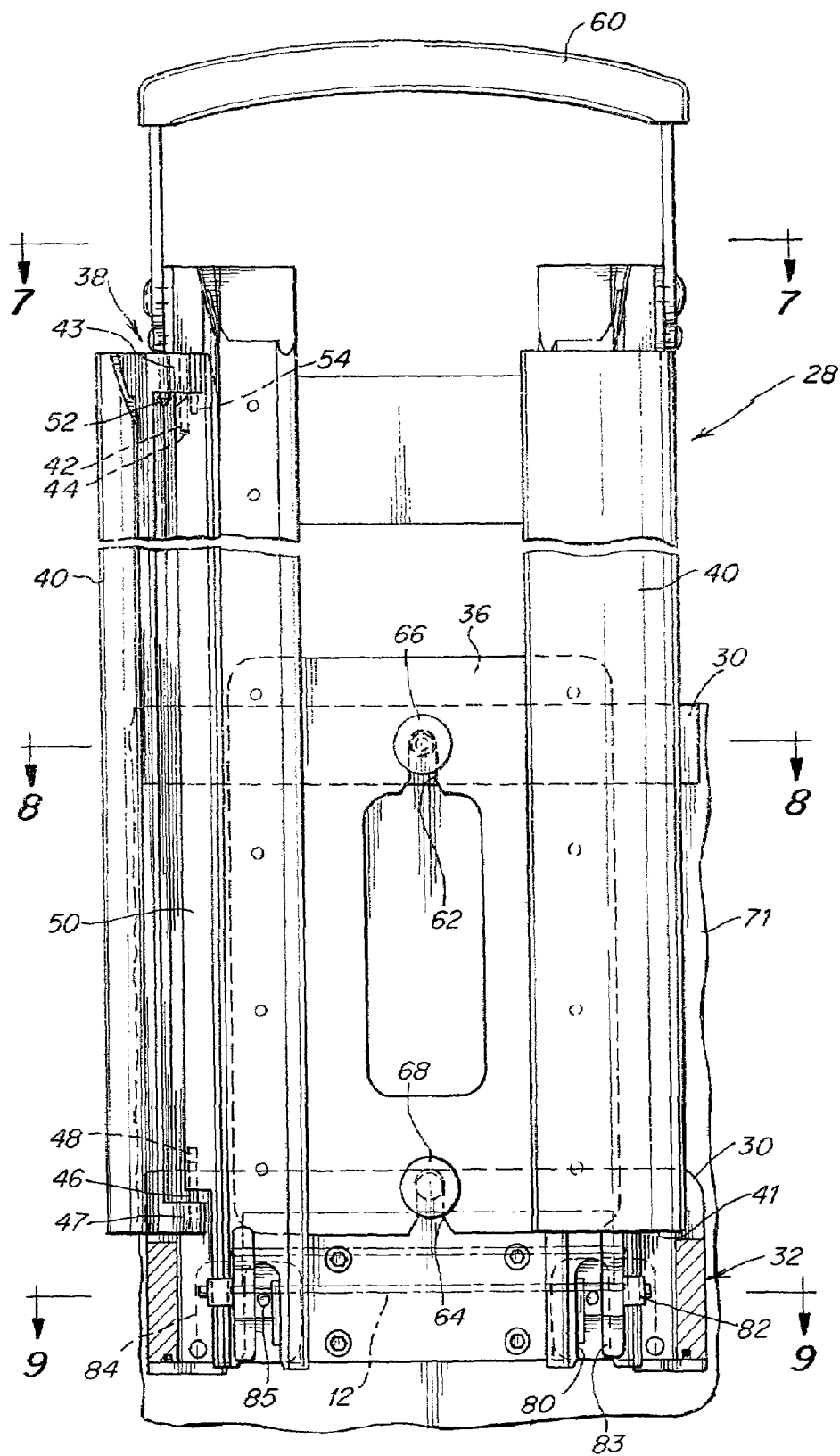
FIG. 6 is a partially broken away, front elevational view of the stacker assembly of this invention as seen along the line 6—6 of FIG. 3.

Column 110 of each plate lifter independently moves in the Z direction (as shown in FIG. 1) with respect to carriage 106, along Z slides 116 (see FIGS. 3 and 5). Columns 110 are driven in the Z direction by Z drive motors 118 and Z belts 120. Details of two exemplary couplings of Z drive motors 118 and belts 120 to associated plate lifters 102 and 104 are illustrated in FIGS. 3 and 5. FIG. 3 illustrates one example with respect to plate lifter 104, while FIG. 5 illustrates another example with respect to plate lifter 102. Like numbers are used for like parts, where applicable. In FIG. 3, belt 120 extends between idler pulleys 115 and over drive pulley 117 which is mounted to Z drive motor 118. Belt 120 is affixed to column 110 by a bracket 113. In FIG. 5, drive pulley 117 is intermediate two idler pulleys 115 and additional idler pulleys 111 are disposed on either side of drive pulley 117. It is understood, of course, that other conventional couplings and drive systems may be used to control movement of plate lifters 102 and 104 in the Z-direction.

Figure 4:
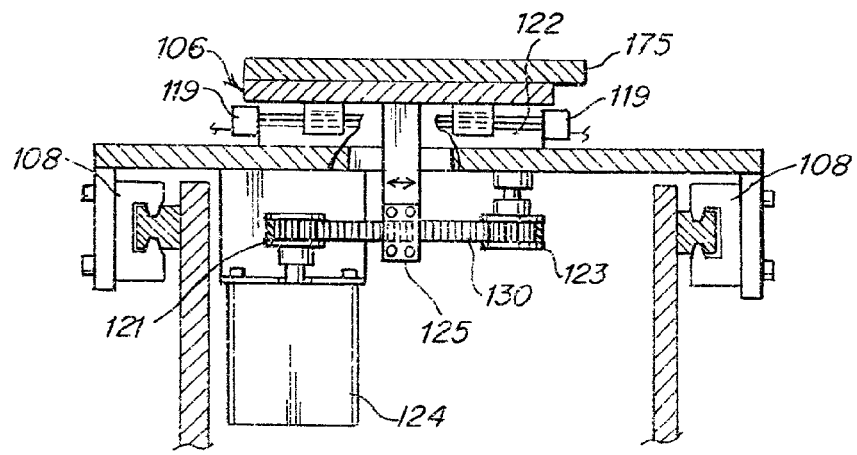
FIG. 4 is a fragmentary, cross-sectional side view of a portion of the pipetting system of this invention taken along the line 4—4 of FIG. 2.

Carriage 106 with plate lifters 102, 103 104 and 105 typically is moved both forward and backward in the Y direction, as shown in FIG. 1, along associated Y slides 122 by Y drive motor 124 and belt 130 (See FIG. 4). An exemplary embodiment of the coupling of Y drive motor 124 and belt 130 to carriage 106 is illustrated in FIG. 4. Belt 130 extends between pulley 121 mounted on motor 124, and pulley 123. Bracket 125 affixes belt 130 to the underside of carriage 106. Y slides 122 include spaced limit sensors 119 which send a signal to processor 292 which in turn controls motor 124 for control of movement of carriage 106 in the Y direction. Pads 112 may be rapidly oscillated, for example, to separate a plate 12 from another plate 12 to which it is stuck in a stacker assembly or to adjust the position of pads 112 in the Y-direction as needed. It is understood of course that conventional couplings and systems may be used to drive and control movement of plate lifters 102, 103, 104 and 105 in the Y-direction and that separate Y drives could be used for each plate lifter 102, 103, 104 and 105.

Z slides 116, Z drive motor 118, Z belt 120 and pulleys 111, 115 and 117 for plate lifters 102, 103, 104 and 105 are all mounted on assembly 100 and move with carriage 106 in the X and Y directions. Similarly, Y drive motor 124, Y drive belt 130 pulleys 121 and 123 and Y slides 122 are also mounted on assembly 100 and travel with carriage 106 in the X direction.

In another, optional feature of this invention, a drip tray 175 is provided on carriage 106 around plate lifters 102, 103, 104 and 105. Drip tray 175 includes a recessed area 177 with inner upstanding walls 179 and outer upstanding walls 181 which contain any liquid which may be spilled during pipetting and washing operations. Columns 110 pass through carriage 106 and are protected and surrounded by inner walls 179 to prevent liquid from entering housing 14 around columns 110.

The stacker assemblies 20, 22, 24 and 26 will now be described with particular reference to FIGS. 1, 2, 3 and 6–15. It is understood, of course, that the number of stacker assemblies could be greater or lesser than four. For example, only two stacker assemblies would be required if a fill station 200 were used in conjunction with system 10. Preferably, two stacker assemblies are disposed on either side of head assembly 500, although other configurations are possible.

Each stacker assembly 22, 22, 24 and 26 is identical in all substantial respects to every other stacker assembly. Therefore, only one stacker assembly will be described, and the reference numbers applied to elements thereof correspond to identical elements in all other stacker assemblies. Each stacker assembly 20, 22, 24 and 26 includes a stacker chimney 28, rear mounts 30 and base assembly 32.

A typical stacker chimney 28 will now be described with particular reference to FIGS. 3 and 6–15. Chimney 28 is sized and shaped to receive plates 12 of different thicknesses. Each chimney 28 includes two spaced, generally parallel side walls 34, back wall 36, and two doors 40. Each door 40 is mounted on an associated side wall 34 about a hinge 38. Is it understood, of course, that doors 40 are optional, and that chimney 28 could have a front opening with no doors, fixed plates in place of doors 40 or one solid wall in place of doors 40. Doors 40, side walls 34 and back wall 36 preferably partially surround plates 12 within chimney 28 and prevent plates 12 from falling out of chimney 28. Preferably, although not necessarily, doors 40, and side walls 34 are each individually and separately formed as a single extrusion. Side walls 34 may be mounted onto back wall 36 such as by a screw, rivet or other like attachment device 41.

Each hinge 38 typically comprises a sidewall section 50 mounted on an associated sidewall 34 and upper hinge section 43 and lower hinge section 47, both of which are mounted on door 40. An upper pin 42 extends downwardly from upper hinge section 43 into a correspondingly formed hole 44 in sidewall section 50. A lower pin 46 extends upwardly from lower hinge section 47 into a correspondingly formed hole 48 in the lower part of section 50. Upper hinge section 43 rests on side wall section 50, while lower hinge section 47 is spaced below the lower end of side wall section 50. A second, shorter pin 52 which is laterally spaced from and general parallel to upper pin 42 also extends downwardly from upper hinge section 43. Pin 52 is configured to reside within hole 54 when door 40 is in its closed position as shown in FIG. 8. The force of gravity retains pins 42 and 52 in their respective holes 44 and 54. However, when it is desired to open door 40, door 40 is manually raised upwardly in a direction generally parallel to pins 42 and 52 until lower hinge section 47 is raised into abutment with the lower edge of side wall section 50. At this point, as shown in FIG. 7A, pin 52 is raised entirely out of its corresponding hole 54, thus permitting pivoting of door 40 in one direction about pins 42 and 46 to move door 40 into the open position as shown on the left hand side of FIG. 7. Opening of doors 40 permits the insertion and retrieval of plates 12 from a chimney 28. Door 40 may be closed simply by again raising door 40 upwardly and by thereafter pivoting door 40 in the opposite direction about pins 42 and 52 from the position shown on the left-hand side of FIG. 7 to the position shown on the right-hand side of FIG. 7. Pin 52 rides on ramped or sloped upper surfaces of sidewall section 50 until pin 52 is again in registration with its associated hole 54. Thereafter, door 40 is released, and pin 52 drops into hole 54 under the influence of gravity.

Side walls 34 are provided with a plurality of rounded ridges 56 which extend generally vertically, or in the direction of movement of plates 12 through chimney 28, along the length of side walls 34. In addition, doors 40 contain rounded, ridges 58, and backwall 36 contains ridges 57, all of which extend parallel to ridges 56. Ridges 56 on opposed side walls 34 are spaced from each other a distance generally equal to the length of a plate 12 to be inserted within chimney 28. Similarly, ridges 57 are spaced from ridges 58 a distance generally equal to the width of a plate 12 to be inserted within chimney 28. Ridges 56, 57 and 58 guide vertical movement of plates 12 within chimney 28 and accommodate imperfections in plates 12 with regard to their size, or shape. Also, frictional contact between plates 12 and chimney 28 is minimized. In this way, plates 12 are guided in relatively frictionless vertical movement within chimney 28, thereby preventing binding of plates 12 within chimney 28.

A handle 60 is pivotally mounted to opposed sidewalls 34 at the top of each chimney 28 and allows the user to manually carry the chimneys 28 with plates 12 therein and to replace one chimney 28 with another as will be described.

The back wall 36 of each chimney 28 comprises at least one and preferably two slots 62 and 64, each having angled guide surfaces feeding into the slot. These slots 62 and 64 are designed to be in registration with associated buttons 66 and 68 mounted on rear mounts 30 which in turn are mounted on housing wall 71. Buttons 66 and 68 support chimney 28, and the provision of two buttons 66 and 68 provides proper alignment of chimney 28. In a preferred embodiment, button 66 includes a compression spring which urges button 66 toward back wall 36 of chimney 28 to hold back wall 36 tightly against rear mount 30 and which facilitates insertion of button 66 into associated slot 62 by providing some play in the position of button 66.

Each chimney 28 is substantially open from top to bottom, to facilitate the free flow of plates 12 vertically through the chimney 28. Also, in one embodiment, the ridges 58 on the inwardly facing edges of door 40 are spaced from one another when doors 40 are in a closed position to provide a vertically extending opening between doors 40 so that a user may reach through the opening and manually grasp and slide a plate or plates 12 upwardly or downwardly in chimney 28. Each chimney 28 preferably, but not necessarily, is tapered at the upper end to facilitate insertion of plates 12 from the upper end. A taper typically is found on doors 40, ridges 56, 57 and 58 and on the upper edges of walls 34 and 36. Side walls 34 typically extend below the lowest edge 41 of doors 40 along each side of chimney 28.

A channel 72 having side walls 76 extends along the length of the interior of each side wall 34 parallel to and between ridges 56. A space between side walls 76 and side wall section 50 accommodates hinge 38 on door 40 when door 40 is in an open position. Disposed at a lower end of each side wall 34 within channel 72, and preferably below the lowest edge 41 of doors 40 is a flap 74. Flap 74 is pivotally mounted within channel 72 about axle 75 that extends into side walls 76 of recess 72. Axle 75 is typically disposed horizontally, or is oriented in a direction generally perpendicular to the direction of movement of plates 12 through chimney 28. Associated with flap 74 and axle 75 is a torsion spring 78 which biases flap 74 into a generally horizontal position, or into an open position in which flaps 74 extend into the interior of chimney 28 beyond channel 72 and beyond ribs 56. In this way, when flaps 74 are in their open position, plates 12 residing within chimney 28 rest on or are caught by flaps 74 and are prevented from passing out through the bottom of chimney 28.

Back wall 36 of chimney 28 also preferably extends below the lowest edge 41 of doors 40. Back wall 36 includes two slots or archways 80 formed in the shape of an upside-down U which extend to the lower edge of back wall 36.

A bracket 82 is affixed to each side wall 34 and includes a section 83 which is disposed on the front of chimney 28 below lowest edge 41 of associated door 40, so that two sections 83 are disposed on the front of chimney 28 below lowest edges 41. Sections 83 prevent plates 12 within chimney 28 from sliding out of chimney 28 below lowest edges 41 while chimney 28 is being transported. Also, bracket 82 may be used to guide and center plates 12 moving downwardly in chimney 28.

Figure 9:
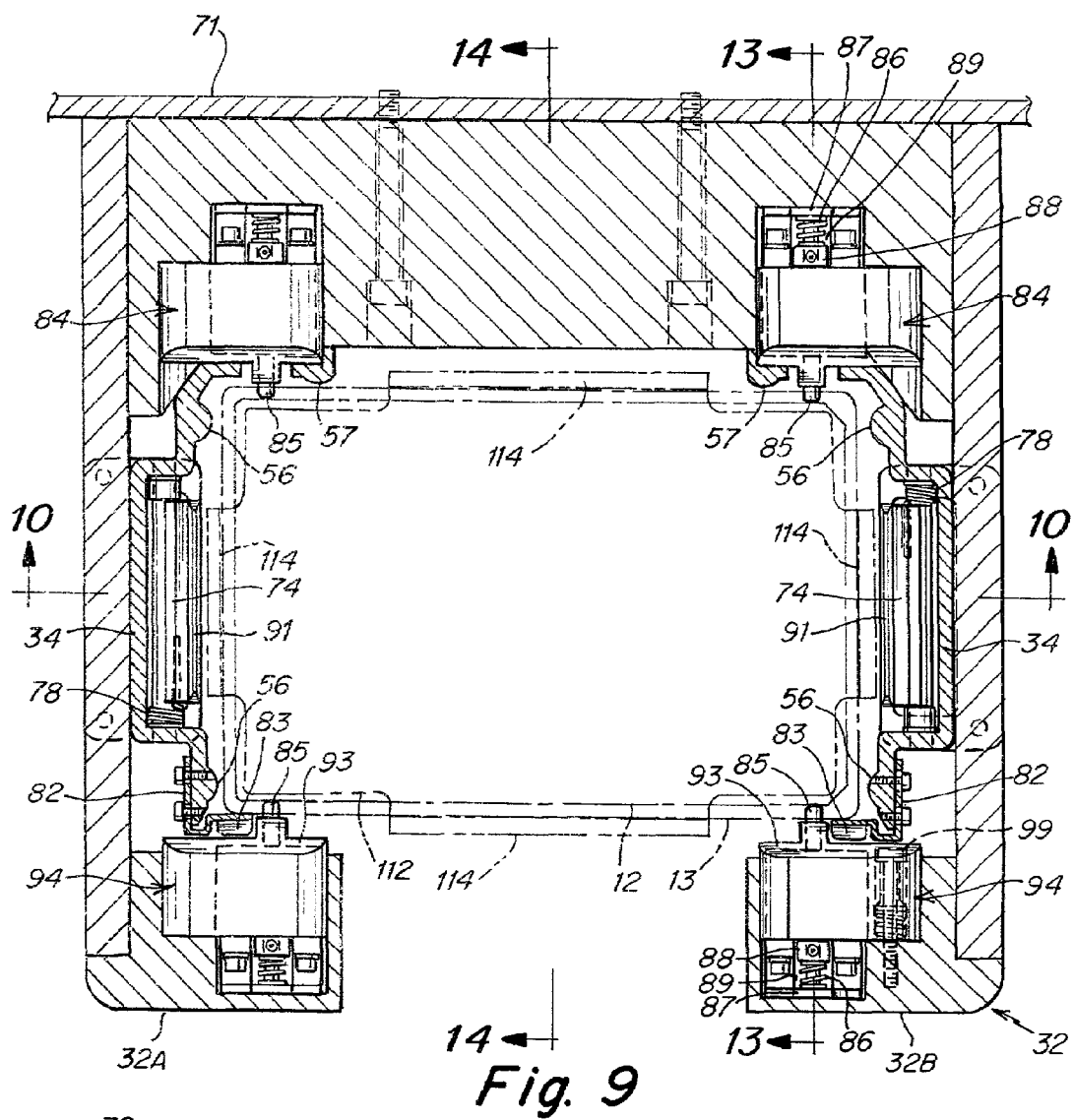
FIG. 9 is a cross-sectional plan view of the stacker assembly of this invention taken along the line 9—9 of FIG. 6.

Base assembly 32 is permanently mounted onto housing wall 71. Base assembly 32 typically includes two arms 32A and 32B, the ends of which are spaced from one another to provide an opening that is an extension of the opening between doors 40 to allow a user to grasp and slide plates 12 within base assembly 32. Base assembly 32 includes a plurality, typically 4, of movable pins or arms 85. These arms 85 are retractable either by a stepper motor or the like (not shown) or by solenoids 84 and 94, which are either electrically or pneumatically actuated, as shown in FIG. 9. Each arm 85 extends from an associated solenoid or motor toward the interior of base assembly 32. Typically, solenoids 84 and 94 are disposed in aligned, opposed, spaced relationship in base assembly 32 as shown in FIG. 9. Preferably, four such solenoids 84 and 94 are employed. Each arm 85 is biased toward the interior of base assembly 32 by a biasing member, such as a compression spring 86 which bears against a spring keeper 87. Solenoids 84 and 94 are slidably disposed on pins 97 which permit adjustment of the position of solenoids 84 and 94 toward and away from the center opening of base assembly 32 using a spring mounted adjustment screw 99 or the like. The spring on screw 99 urges the solenoid 84 and 94 toward the center opening. This feature allows base assembly 32 to accommodate plates 12 of different sizes. Solenoids 84 and 94 are actuated by processor 292 to withdraw the distal ends of arms 85 from within the interior of chimney 28 so that the distal ends of arms 85 do not project beyond ridges 57 and 58. This actuation allows an assembly to accept and dispense plates 12 through its lower end, as will be described. Each solenoid 84 and 94 includes an upper, sloped surface 93 which typically extends into the center opening beyond respective ridges 57 and 58 and which guides the plates 12 into position in the center of base assembly 32 and into engagement with arms 85. As is apparent, the position of a surface 93 on a solenoid is adjusted when the position of its associated solenoid 84 or 94 is adjusted.

Figure 13:
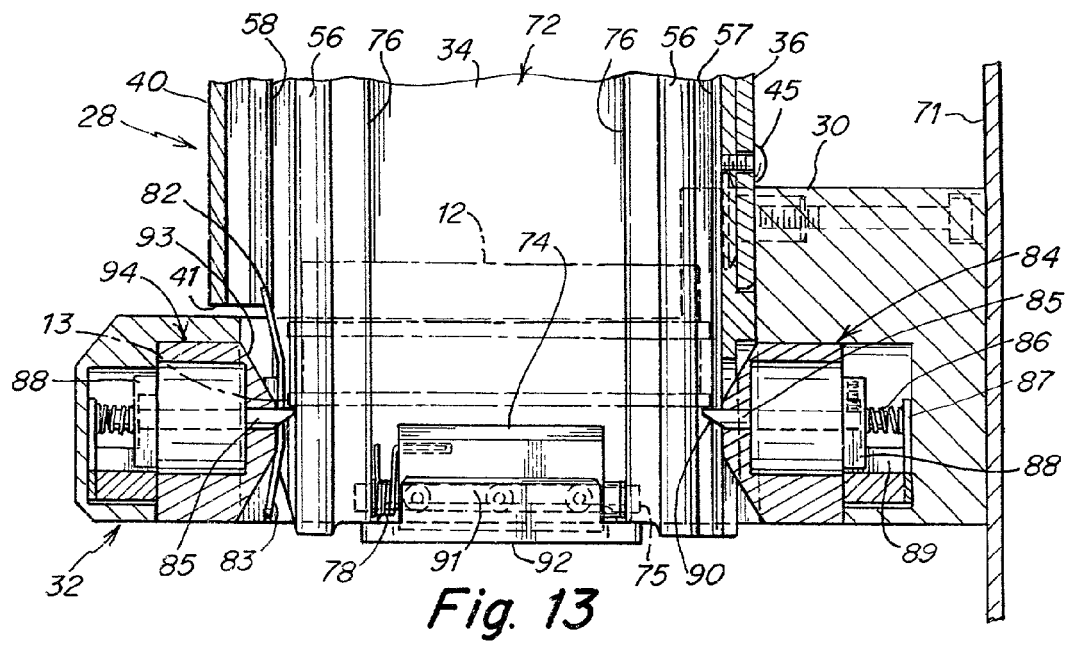
FIG. 13 is a cross-sectional side view of the stacker assembly of FIG. 6 taken along the line 13—13 of FIG. 9.
Figure 14:
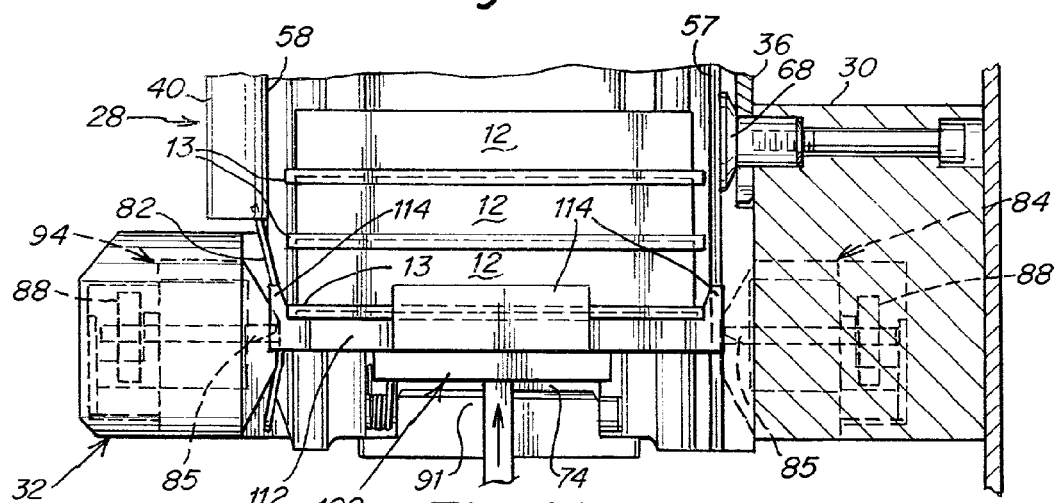
FIG. 14 is a cross-sectional side view of the stacker assembly of FIG. 6 taken along the line 14—14 of FIG. 9 illustrating removal of a plate.
Figure 15:
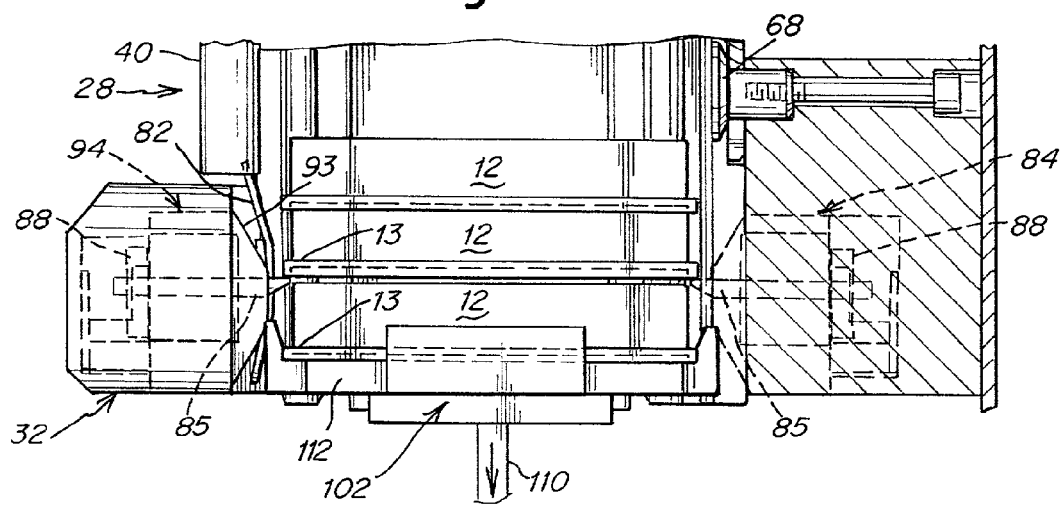
FIG. 15 is a cross-sectional side view of the stacker assembly of FIG. 6 taken along the line 14—14 of FIG. 9 further illustrating removal of a plate.

Plates 12 are individually removed by a plate lifter 104 by first lifting the stack and then by retracting arms 85 of solenoids 84 and 94 as shown in FIG. 14 and thereafter by quickly lowering the stack, and with a predetermined timing, by releasing arms 85 once lip 13 of the lower plate 12 passes and before the lip 13 on the next plate 12 passes to allow springs 86 to return arms 85 to an extended position which allows lip 13 on the next plate 12 to be supported by arms 85. When plates 12 are inserted from below, plate lifter 104 raises the stack off arms 85 first and then arms 85 are withdrawn until the new plate 12 is lifted above solenoids 84 and 94. Once a new plate 12 passes upwardly, arms 85 are released to catch a lip 13 on lowest plate 12, as the stack is lowered, as shown in FIG. 13 to prevent plates 12 from falling out of the bottom of base assembly 32.

In a preferred embodiment, the distal end of each arm 85 extending into the interior of base assembly 32 is beveled, with beveled surface 90 facing downwardly. It is desirable to maintain beveled surface 90 in a downwardly-facing direction to facilitate receipt by assembly 32 of plates 12 from below, when chimney 28 is mounted in base assembly 32. The bevel on arms 85 also allows the arms to extend into the small spaces below a lip 13 on the next lowest plate 12 and above the top of the lowest plate 12 as the lowest plate 12 is removed by a plate lifter 102 or 104 to allow removal of just one plate 12 at a time. The bevel on arms 85 also allows a plate 12 being inserted from below to push arms 85 out of the way as the stack is being raised. Maintenance of beveled surface 90 in a downwardly facing direction is accomplished by preventing rotation of arms 85 in solenoids 84 and 94. Disposed between spring 86 and each solenoid housing is a flag 88 which is mounted to arm 85 by a set screw or the like and which travels in a channel 89 to prevent rotation of arm 85.

Each base assembly 32 also includes a pair of spaced, upstanding walls 91 which extend upwardly from bottom surface 92. Walls 91 are positioned such that when chimney 28 is aligned with and installed on base assembly 32, walls 91 are disposed below flaps 74, but spaced from torsion spring 78, to pivot flaps 74 upwardly about axle 75 and into a vertical orientation parallel to walls 34 and within channel 72. This positioning of flaps 74 when chimney 28 is installed in base assembly 32 allows the plates 12 to be supported only by arms 85 so that movement of plates 12 into and out of each stacker assembly is controlled only by solenoids 84 and 94 without interference from flaps 74.

The installation and removal of chimney 28 from an associated base assembly 32 will now be described with particular reference to FIGS. 6 and 10–13. Chimney 28 may be carried manually to and from base assembly 32 by handle 60. Chimney 28 may be loaded with plates 12, or it may be empty. If loaded with plates 12, the lowest plate 12 rests on flaps 74 which are biased by torsion spring 78 into their open position or into a position in which they extend into the interior of chimney 28. Flaps prevent plates 12 from falling out the bottom of chimney 28. Plates 12 are held in position by ribs 56, 57, and 58. Doors 40 are held in their closed position by pins 52 which are in registration with associated holes 54 to secure plates 12 within chimney 28. Sections 83, which are disposed below lower edges 41 of doors 40, prevent plates 12 from sliding out the front of chimney 28 below doors 40. In this manner, plates 12 are securely held within chimney 28 without fear of loss of plates or fluid.

When installing a chimney 28 in its associated base assembly 32, button 66 is aligned below slot 62, and button 68 is aligned below slot 64 with back wall 36 flush against rear mounts 30. Chimney 28 is then urged downwardly so that button 68 rides into slot 64, and button 66 rides into slot 62. As this is happening, associated arms 85 of solenoids 84 are aligned with the openings of slots 80 and ride into slots 80. Arms 85 on solenoids 94 are also advancing toward lowest edges 41 of doors 40.

Figure 10:
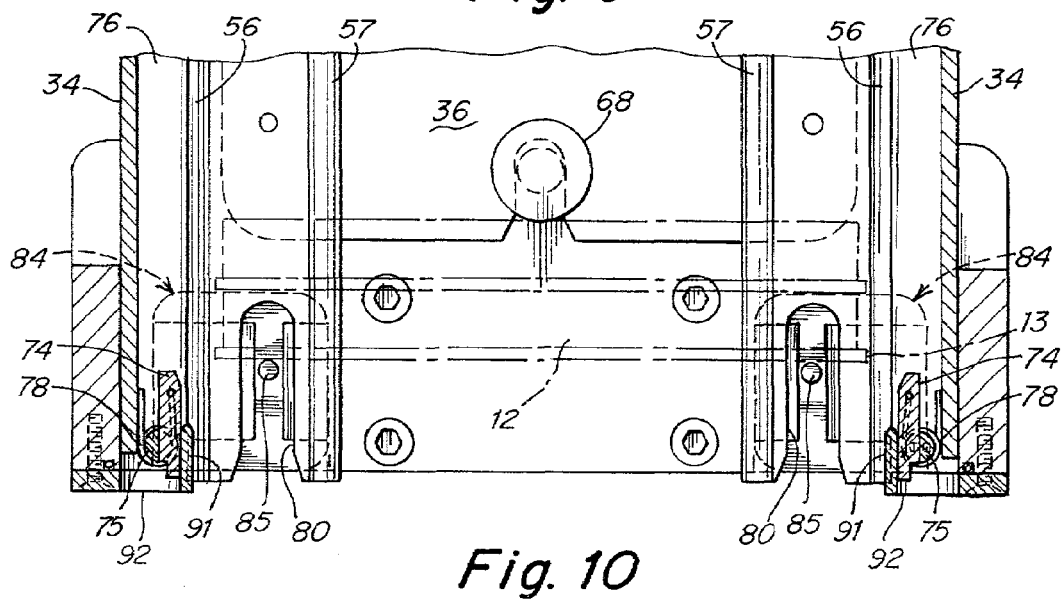
FIG. 10 is a cross-sectional front view of the stacker assembly of FIG. 6 taken along the line 10—10 of FIG. 9.
Figure 11:
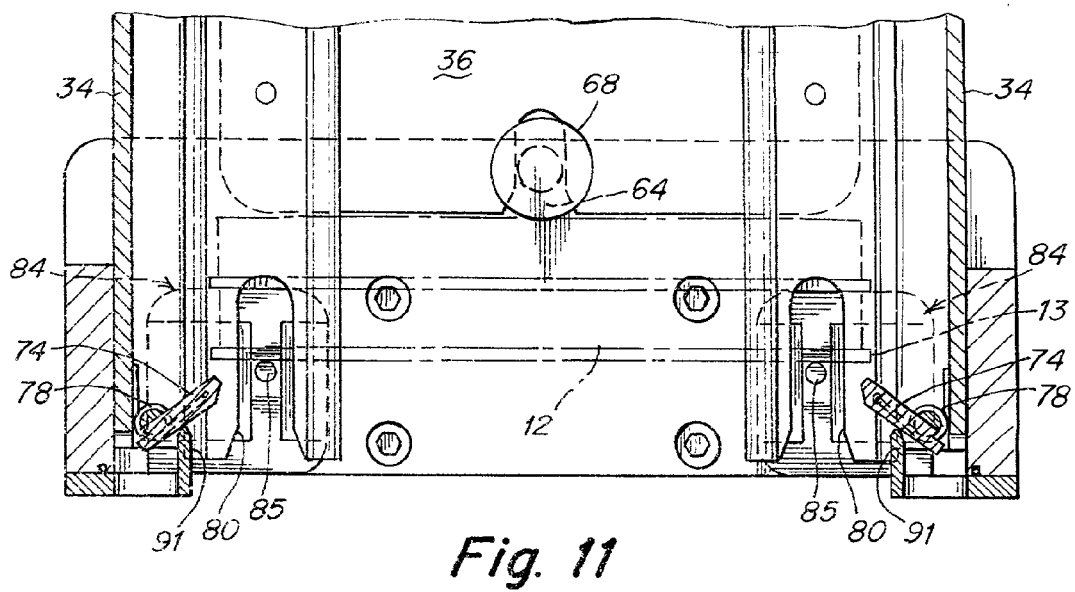
FIG. 11 is a cross-sectional front view of the stacker assembly of FIG. 6 showing removal of the chimney.

Simultaneously with the foregoing, flaps 74 are engaged by upstanding walls 91, as shown in FIG. 11, causing flaps 74 to pivot upwardly against the biasing effect of torsion spring 78 until flaps 74 are in a generally vertical position generally parallel to walls 34 as shown in FIG. 10 (in which stacker chimney 28 is fully seated within base assembly 32). While flaps 74 are being pivoted upwardly, the distal ends of arms 85 of solenoids 84 and 94 are engaging lip 13 on the lowest plate 12 within chimney 28, and raising the lowest plate 12, and all of the other plates 12 stacked on top thereof, upwardly with respect to chimney 28 and away from flaps 74 to allow flaps 74 to pivot upwardly into the position shown in FIG. 10. When fully pivoted, as shown in FIG. 10, flaps 74 reside fully within channels 72 in side walls 34 so that they are completely spaced away from any plates 12 disposed within chimney 28.

Figure 12:
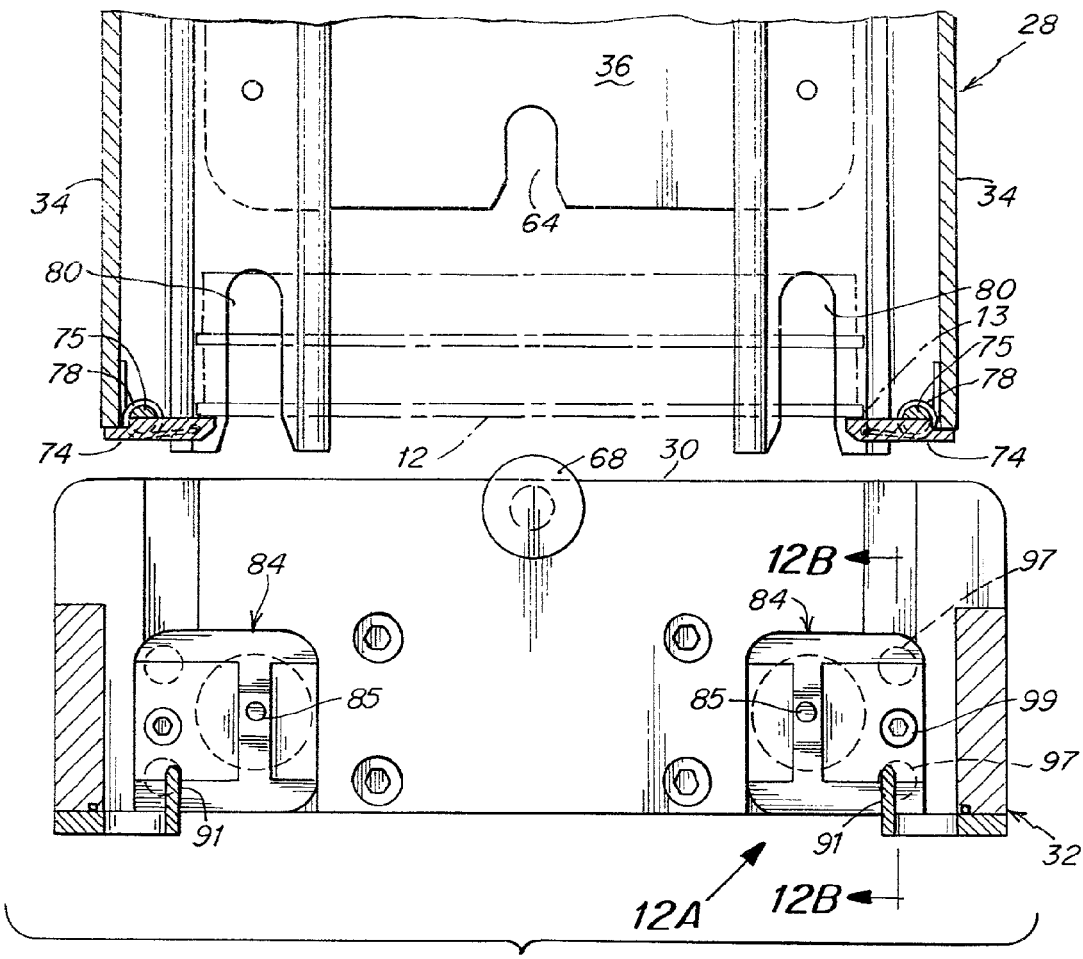
FIG. 12 is an exploded, cross-sectional front view of the stacker assembly of FIG. 6 with the chimney removed.
Figure 12A:
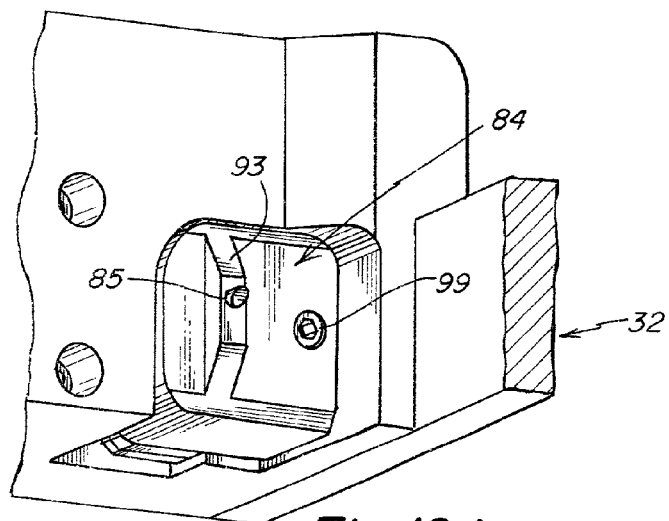
FIG. 12A is a fragmentary, bottom perspective view as seen along arrow 12A of FIG. 12.
Figure 12B:
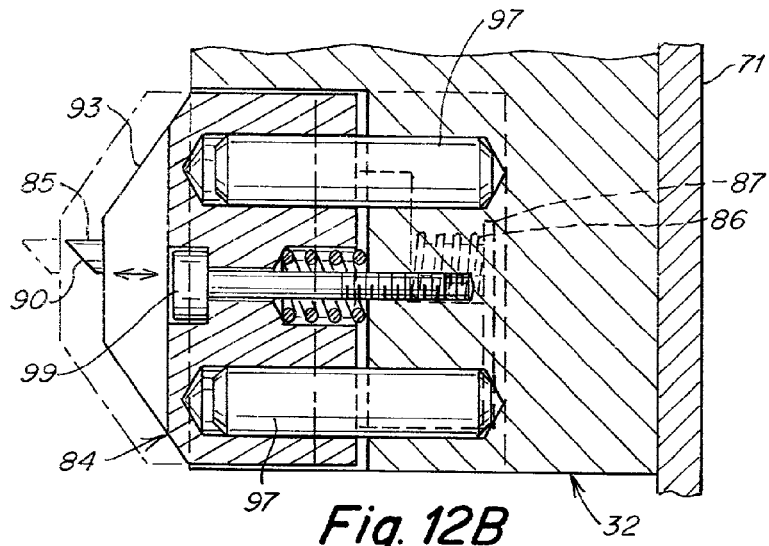
FIG. 12B is a cross-sectional side view taken along the line 12B—12B of FIG. 12.
Figure 12C:
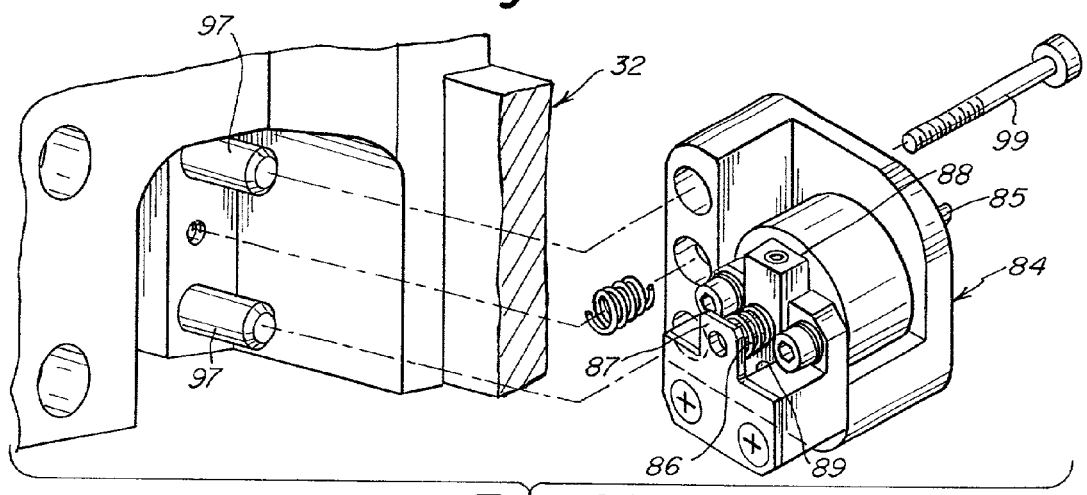
FIG. 12C is an exploded, perspective view of the solenoid shown in FIG. 12.

When a chimney 28 is removed from its associated base assembly 32, the reverse occurs. Namely, as chimney 28 is raised, flaps 74 are raised above upstanding walls 91, thus allowing springs 78 to pivot flaps 74 into their open or generally horizontal position in which flaps extend into the interior of chimney 28. At the same time, arms 85 of solenoids 84 and 94 move downwardly with respect to chimney 28. Arms 85 of solenoids 84 and 94 pass down through the openings of slots 80, as shown in FIG. 11. At about the point where arms 85 of solenoids 84 and 94 are generally even with flaps 74, flaps 74 are already in their open position and thus engage lip 13 of lowest plate 12, to prevent plates 12 from passing through the bottom of chimney 28, as shown in FIG. 12. At this same time, buttons 66 and 68 pass downwardly and out of respective slots 62 and 64 to allow complete removal of chimney 28 from base assembly 32.

Pipetting head assembly 500 will now be described with particular reference to FIGS. 16–20. Head assembly 500 includes a housing 502 which is mounted on housing wall 71, and at least one pipetting head 600 and tray 700. Head 600 is normally mounted in housing 502, but is removable, as will be described, for repair or replacement thereof. Moreover, tray 700 is removable from housing 502 separately from head 600 to allow replacement of the pipette tips 702 disposed therein.

Housing 502 includes a top wall 506 and side walls 508. Disposed on the lower end of each side wall 508 is a block 510 with a plurality of slideways for accepting head 600, as will be described. Extending between block 510 and top wall 506 are a plurality, typically four, of guide shafts 512 which guide vertical movement of generally horizontal plate 514. Plate 514 is moved in a generally vertical direction, or in a direction perpendicular to plate 514 by at least one, and preferably two threaded shafts 516, each of which passes through a nut or other fixture 518 which is mounted on plate 514, and which has a correspondingly threaded interior channel through which associated shaft 516 passes in threaded engagement. The upper end of each shaft 516 is coupled to an associated pulley 520. A motor 522 such as a servo motor or stepper motor, typically mounted behind housing 502, includes a shaft 524 extending from the rotor which has a pulley 526 mounted thereon. A belt 528 extends about pulleys 520 and 526. In this manner, each shaft 516 is rotated in synchronization with the other by motor 522 to raise and lower plate 514 with respect to housing 502. It should be understood that motor 522 may be coupled to shafts 516 by other well known means such as by gears and a chain or the like. Multiple coupling means, or multiple motors may also be used, so long as the movement of both shafts 516 is synchronized.

In one embodiment, disposed on the outside surface of each side wall 508 is a side bracket 530. Each bracket 530 includes an upper wall 532 and a lower wall 534 which extends at generally right angles to upper wall 532 toward tray 700, and which is disposed below block 510. Upper wall 532 is mounted to block 510 by screws or other like fasteners 536 which travel in elongated slots 538 of upper wall 532 to guide vertical movement of bracket 530 with respect to side walls 508 and block 510. Each bracket 530 is biased into a normally up position in which lower wall 534 is urged against the lower surface of tray 700 by a biasing mechanism, such as extension springs 540. While four springs 540 are disclosed for each bracket 530, either a fewer or greater number of springs 540 may be used depending upon the desired biasing force, and the force of each spring. Moreover, while springs 540 are preferred, it is understood that other biasing mechanisms such as pneumatic or electrical cylinders or the like may be utilized. It is understood, of course, that the biasing mechanism for each bracket 530 should apply a substantially identical biasing force. Springs 540 extend between posts 542 mounted on side wall 508 and ledge 544 of each bracket 530, which typically extends horizontally or at right angles to side wall 532 and away from side wall 508.

Mounted on upper wall 532 of each bracket 530 are pegs 546. While two pegs 546 are shown for each bracket, it is to be understood that a single peg 546, or more than two pegs 546 may be utilized. Pegs 546 typically are threadably or otherwise mounted onto upper wall 532 and extend through side wall 532 and into elongated slots 548 in adjoining side wall 508. Pegs 546 extend sufficiently far through associated side wall 508 so that distal ends thereof are disposed below a lower surface of plate 514. If plate 514 is lowered sufficiently with respect to side walls 508, the lower surface of plate 514 will engage pegs 546, pushing pegs 546 and thus associated brackets 530 downwardly with respect to block 510 to urge lower wall 534 away from the lower surface of block 510, against the upward bias of springs 540. As plate 514 is raised out of engagement with pegs 546, springs 540 also raise brackets 530 until lower wall 534 is in engagement with the lower surface of tray 700.

Housing 502 includes upper and lower limit switches 550 and 560 respectively. Upper limit switch 550 indicates when plate 514 is in its uppermost, permitted position. Switch 550 includes two, spaced sensor elements 552 disposed on top wall 506 and a trigger 554 mounted on block 556 which is in turn mounted on plate 514. Lower limit switch 560 indicates when plate 514 is in its lowermost, permitted position, and includes spaced sensing elements 562 mounted on housing 502 and a trigger 564 mounted on block 566 which is in turn mounted on plate 514. Both switches are coupled to processor 292 to control motor 522.

Figure 16A:
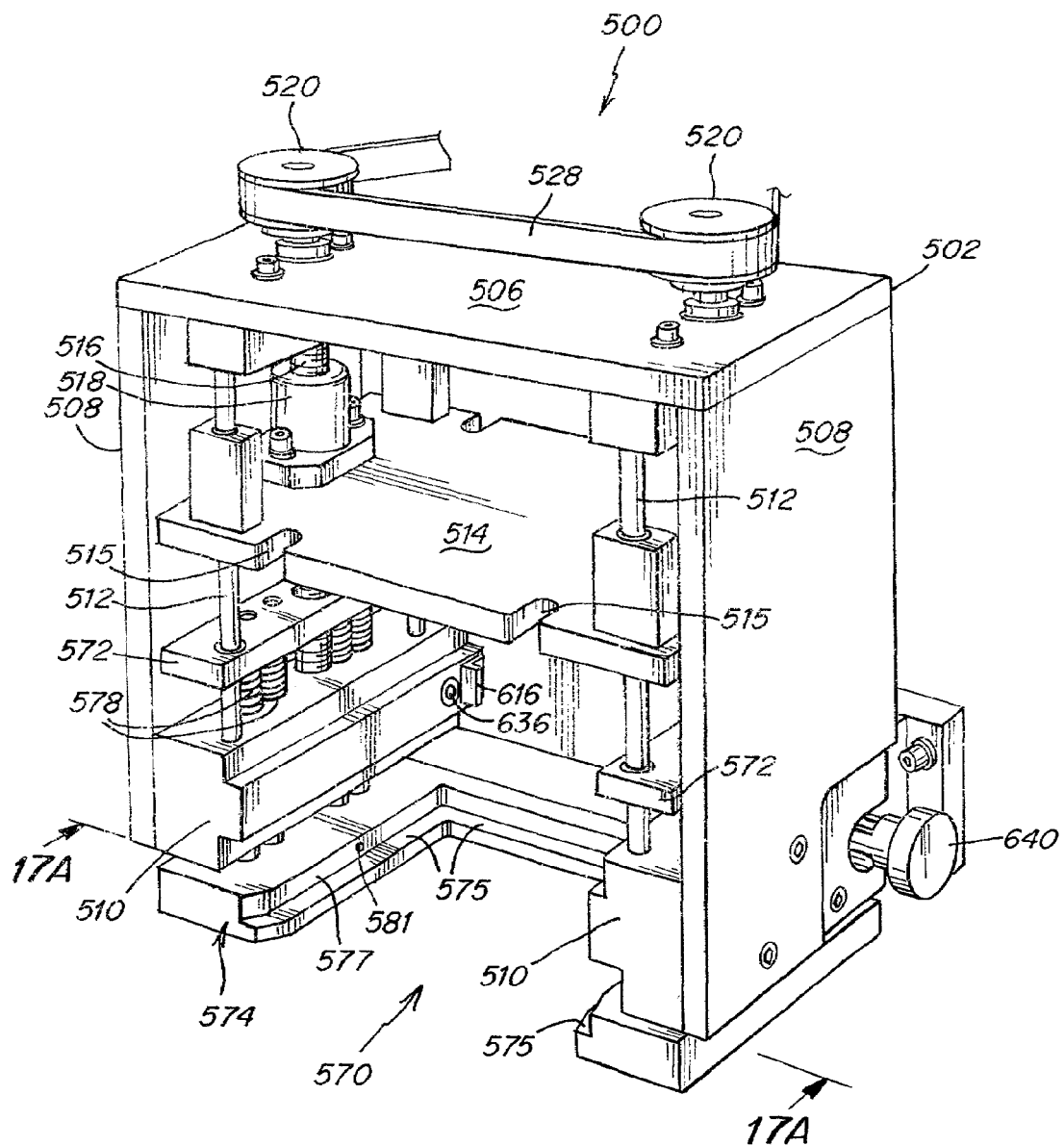
FIG. 16A is a perspective view of an alternative embodiment of the head assembly of FIG. 16.
Figure 17:
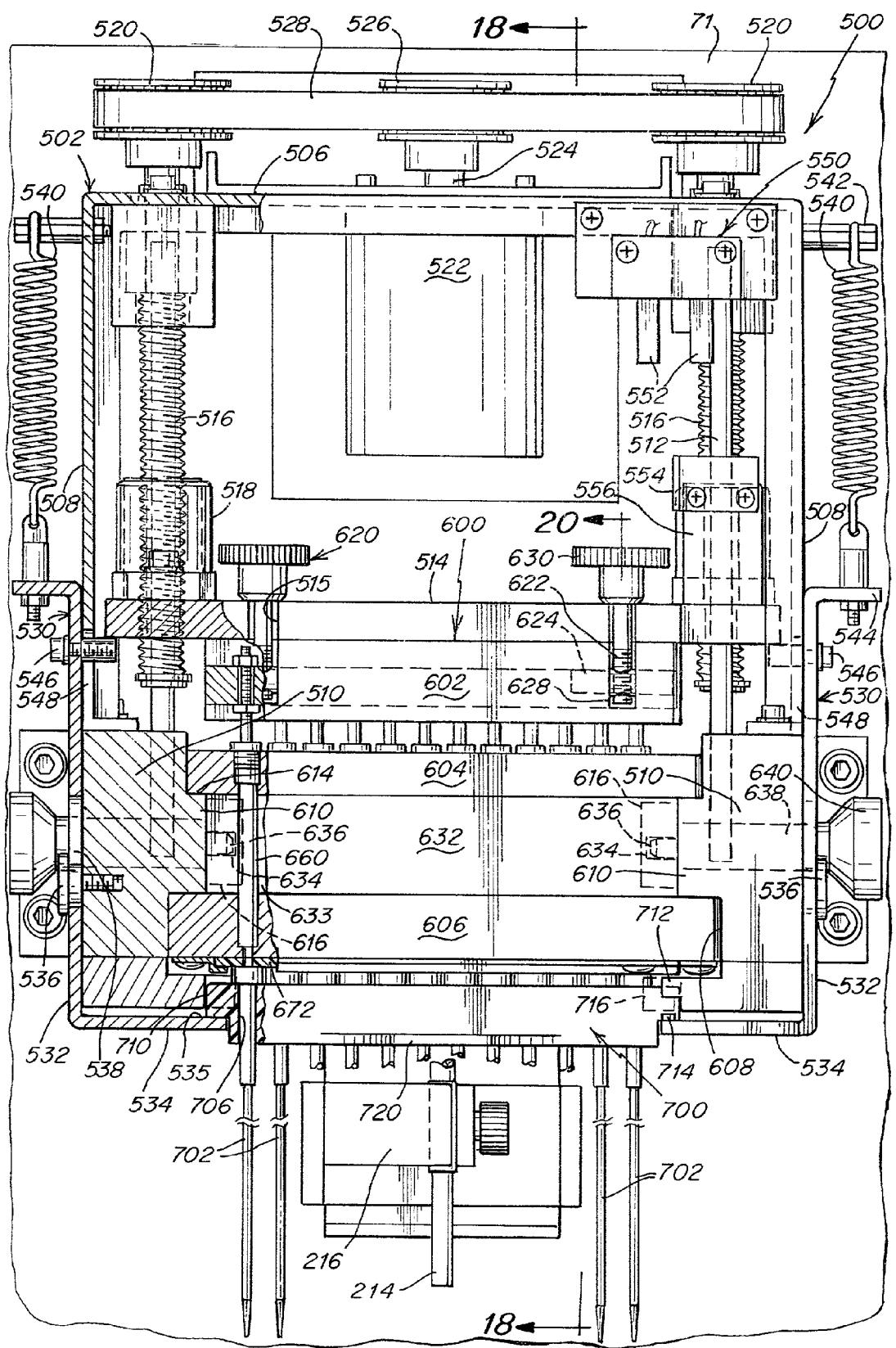
FIG. 17 is a partial cross-sectional, front elevational view of the head assembly as seen along the line 17—17 of FIG. 16.
Figure 17A:
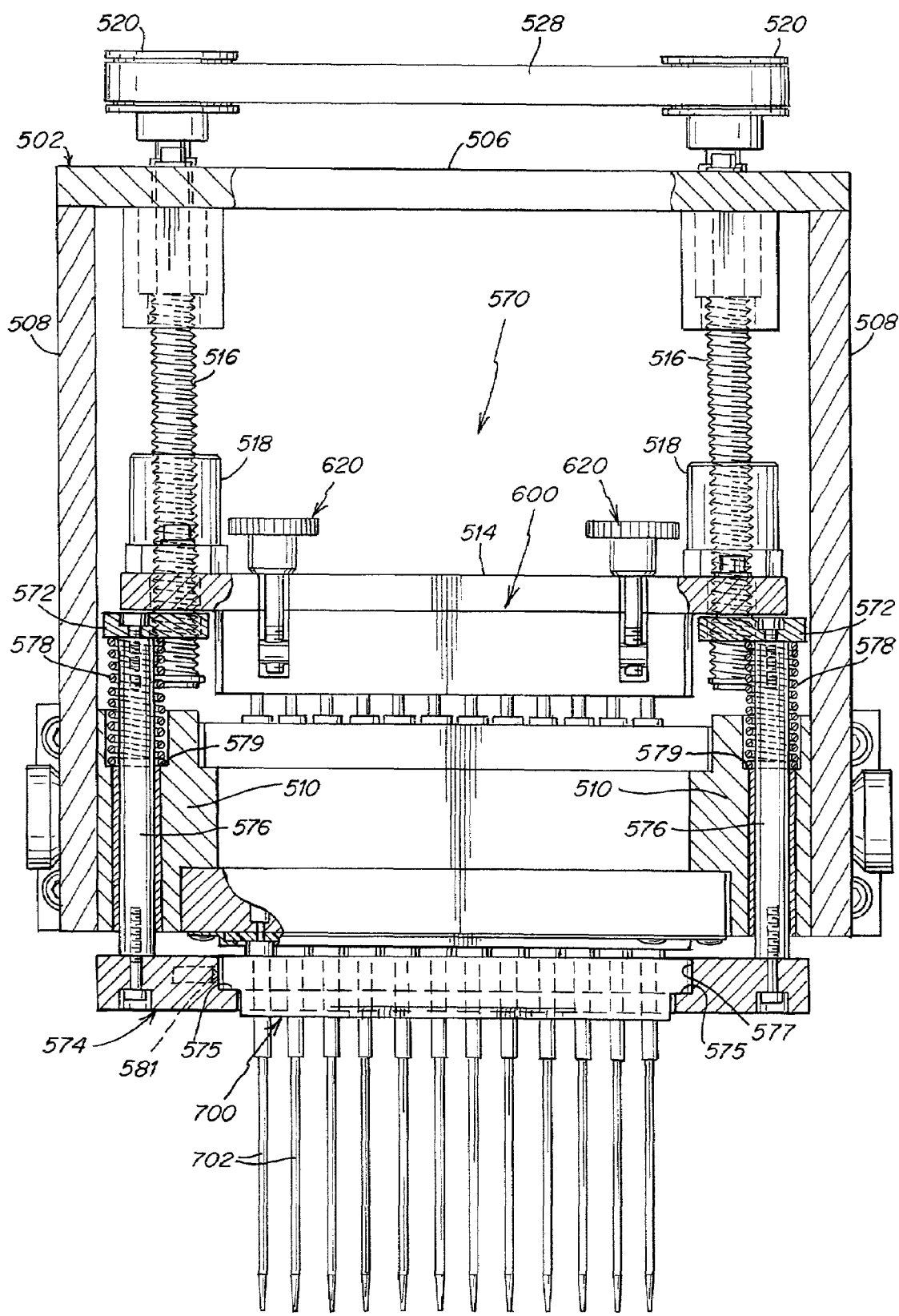
FIG. 17A is a partially broken away, front, elevational view, as seen along line 17A—17A of FIG. 16A.
Figure 18:
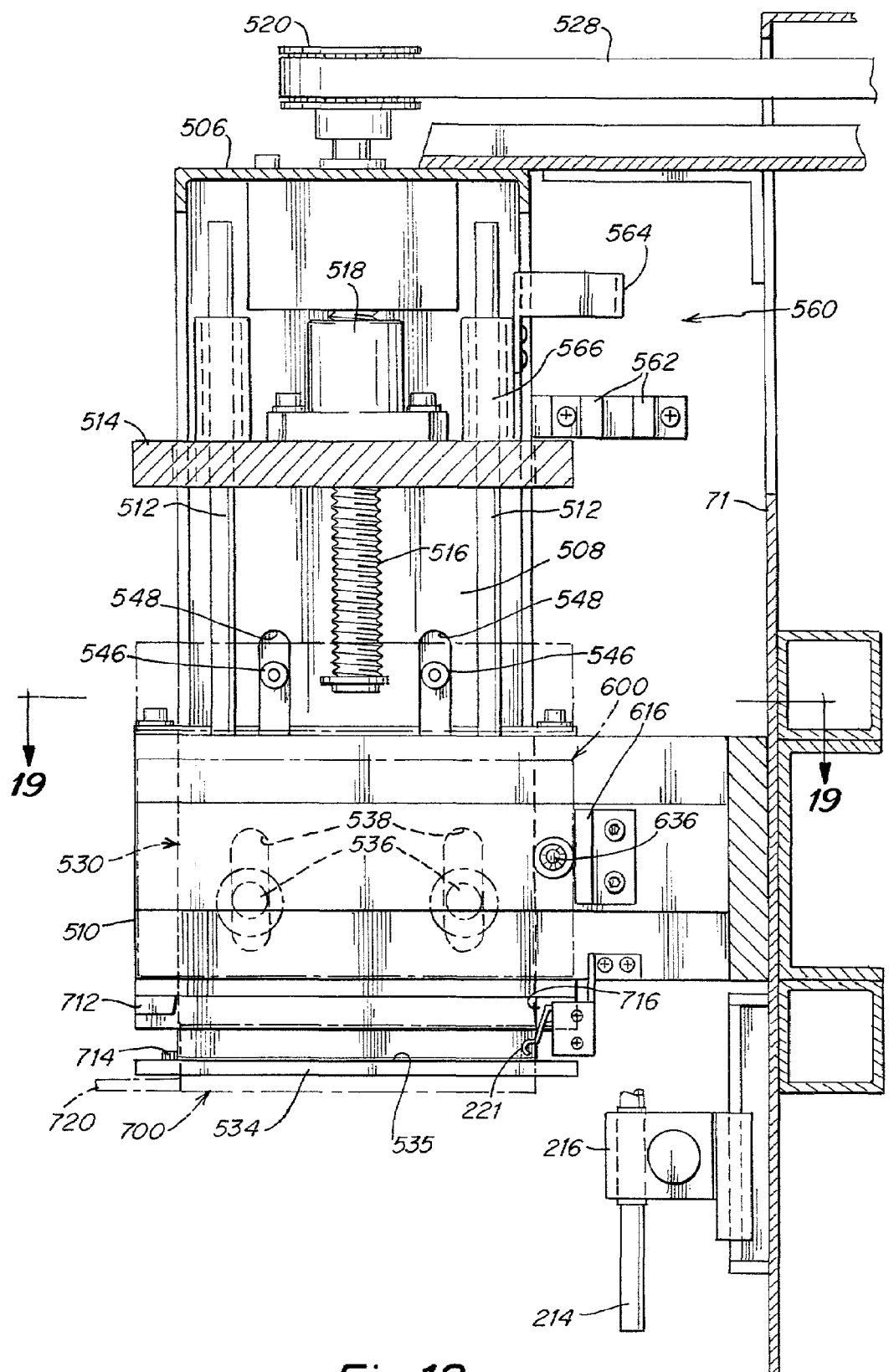
FIG. 18 is a partial, cross-sectional side view of the head assembly of this invention taken along the line 18—18 of FIG. 17.
Figure 19:
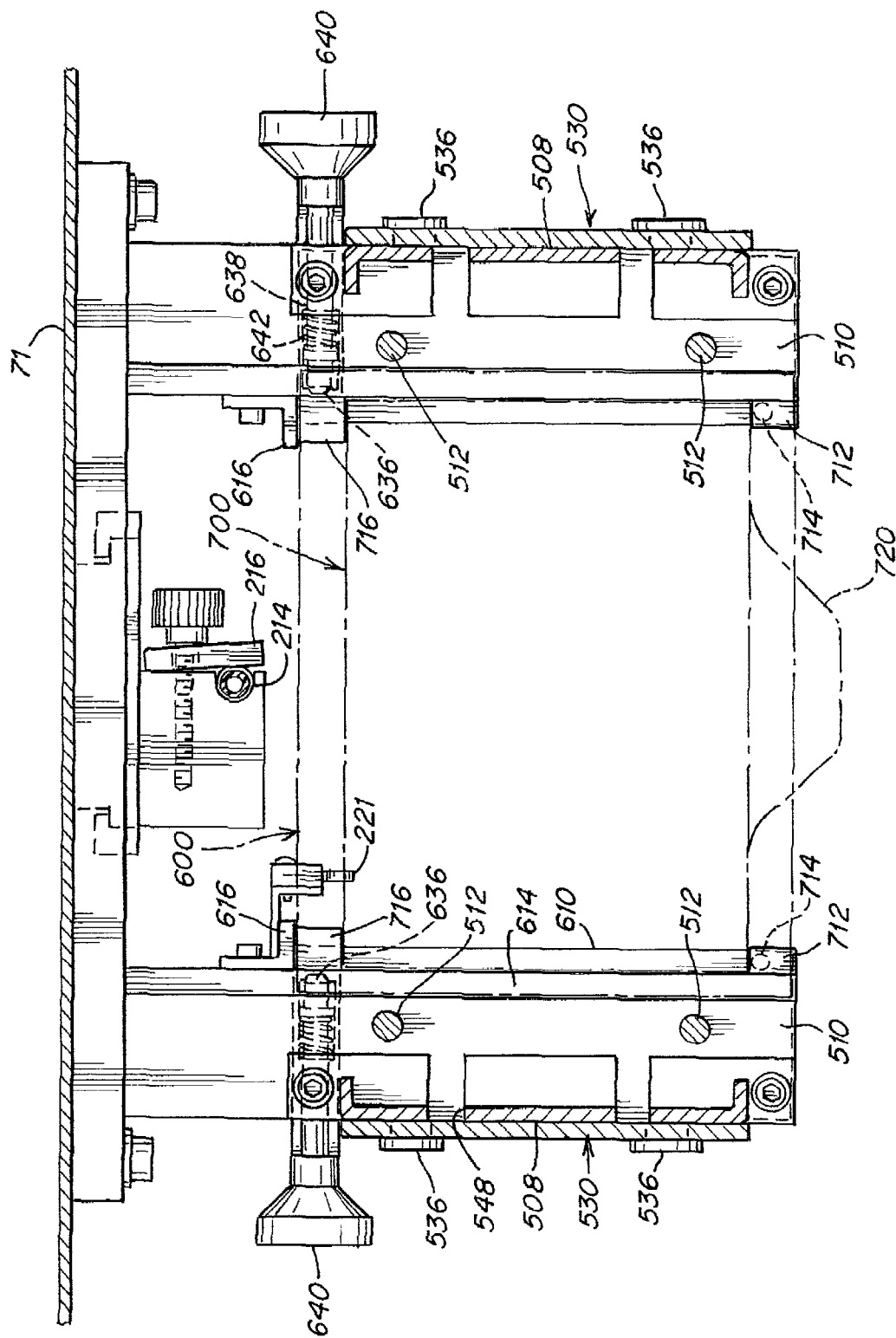
FIG. 19 is a partial, cross-sectional plan view taken along the line 19—19 of FIG. 18.

An alternative embodiment of pipetting head assembly 500 will now be described with particular reference to FIGS. 16A and 17A. Like numbers are used for like parts, where appropriate. The primary difference between the embodiment of FIG. 16, and the alternative embodiment of FIG. 16A, is that brackets 530 have been eliminated in FIG. 16A, and the same result is produced by a mechanism 570 mounted internally of housing 502 which performs substantially the same function as brackets 530 and springs 540. Mechanism 570 includes a pair of upper plates 572 which are mounted within housing 502, a clamp 574 disposed below block 510, a plurality of shafts 576 and biasing members, such as springs 578. Plates 572 are disposed generally parallel to plate 514 and move within housing 502 along guide shafts 512 below plate 514. It is to be noted that shafts 512 are anchored in block 510 and top wall 506 just as in the embodiment of FIG. 16. Plates 572 are disposed on opposite sides of housing 502. Plates 572 typically are no wider than the upper end of block 510 to accommodate head 600. Each shaft 516 driven by motor 522 passes through a corresponding, non-threaded hole in an associated plate 572 without engagement of plate 572. A plurality, for example four, of shafts 576 extend from each plate 572 through block 510 on an associated side of block 510 and into an associated side of clamp 574 where shafts 576 are anchored. Surrounding each shaft 576 is a coiled compression spring 578 which on one end bears on a lower surface of an associated plate 572 and, at the opposite end bears on a bearing surface 579 in block 510. Bearing surface 579 may be either on the top surface of block 510, or within block 510 on a lip in the hole through which shaft 576 extends. In this embodiment, clamp 574 has clamping surfaces 575 and upstanding walls 577 that extend around three sides of clamp 574, one side adjacent each set of shafts 576, and a third side along a back surface of housing 502. Clamping surfaces 575 serve to clamp a tray 700 against head 600. In one embodiment, a spring loaded, ball detent 581 is disposed on one side wall 577 of clamp 574 to help align a tray 700 by pushing tray 700 against wall 577 on the opposite side of clamp 574.

The operation of the embodiment of FIGS. 16A and 17A will now be described. Springs 578 bear against bearing surfaces 579 and against plates 572 to urge plates 572 upwardly with respect to housing 502. Such motion also urges shaft 576 upwardly, urging clamp 574 against tray 700. When it is desired to lower clamp 574, plate 514 is lowered, as previously discussed by operation of motor 522 which rotates threaded shafts 516. As plate 514 is lowered, it engages plates 572, urging both of plates 572 downwardly toward clamp 574, in much the same manner as plate 514 pushes brackets 530 downwardly. Plates 572 are pushed downwardly against the upward bias provided by springs 578. When plate 514 is lowered a predetermined amount, clamp 574 is spaced sufficiently below block 510 to allow insertion and removal of tray 700. The process is reversed after insertion of tray 700 for clamping of tray 700 against head 600. Because clamping surfaces 575 extend around three sides of tray 700, tray 700 is securely clamped within head 600. Moreover, upstanding walls 577 which extend upwardly from clamping surfaces 575 assist in orienting and aligning tray 700. When clamp 574 is raised upwardly to urge tray 700 against head 600, tray 700 is clamped tightly against the bottom surface of head 600, as will be described, and head 600 is also clamped into place. Ball detent 581 forces tray 700 to be pushed to one side of clamp 574 for consistent positioning of tray 700 regardless of dimensional tolerance variations in tray 700. As shown in FIG. 16A, detent 581 pushes tray 700 against the wall 577 on the right side of clamp 574.

Head 600 will now be described with particular reference to FIGS. 16–20. Head 600 is configured to slide into and out of block 510, as illustrated in FIG. 16. Head 600 preferably includes three, closely-spaced and generally parallel plates 602, 604 and 606. Lowermost plate 606 is configured to be introduced into block 510 along slideways 608. Slideways 608 include an upper, protruding lip 610 which is configured to engage an upper surface of lower plate 606. Slideways 608 also include a lower surface 612 upon which a lower surface of plate 606 rests. Plate 604 is configured to slide on slideway 614 of block 510. Stops 616 are disposed within block 510 to limit movement of head 600 into housing 502 to permit proper alignment and positioning of head 600. Slideways 614 and 608 are spaced the same distance apart as are plates 604 and 606. Connectors 632 and 633 couple plates 604 and 606 and fix the position of plate 604 with respect to plate 606.

Upper plate 602 includes a plurality, typically four attachment devices 620 which are configured to secure plate 602 and thus head 600 to plate 514. Each attachment device 620 includes a threaded shaft 622 which is mounted on a pin 624 which is rotatably mounted in block 626 of upper plate 602. A cutout 628 in block 626 permits rotation of shaft 622 about pin 624 from a generally horizontal or slightly below horizontal position to a generally vertical position. Disposed on the protruding end of each shaft 622 is a threadably mounted knob 630. When head 600 is disposed in block 510, devices 620 may be pivoted to bring shafts 622 into a generally vertical orientation, so that shafts are received in cutouts 515 in plate 514. Knobs 630 may then be rotated to screw knobs 630 into tight engagement with the upper surface of plate 514. It will be appreciated that the outer diameter of knobs 630 must be greater than the width of cutouts 515 to permit knobs 630 to engage the upper surface of plate 514. Head 600 may be removed simply by unscrewing knobs 630 and allowing them to pivot into a non-vertical position out of cutouts 515 to allow withdrawal of head 600.

The ends of connectors 632 and 633 are recessed to accommodate slideways 614. Disposed on each end of connector 633 is a recess 634 which is configured to receive the tip 636 of a spring-loaded connector pin 638 which projects through block 510. Each pin 638 includes a knob 640 to allow manual grasping and withdrawal thereof, and an extension spring 642 which biases pin 638 into recess 634 when head 600 is in position within block 510 against stops 616. Pins 638 align and hold head 600 in place within housing 502.

As illustrated in FIG. 20, head 600 includes a plurality of fluid withdrawal mechanisms 650. The number of such mechanisms corresponds to the number of tips 702 in tray 700. Typical examples include an array of 96 or 384 mechanisms 650. The number of tips 702 may correspond to the number of wells 11 in a plate 12 to be pipetted, or the number of tips 702 may be some known fraction of the number of wells 11. Each mechanism 650 includes a piston tube 660 having a piston rod 652 which is securely affixed at an upper end to plate 602. One means of affixation could include, for example, a pair of nuts 654 and 656 which are threaded onto a correspondingly threaded end of piston rod 652. It should be understood that other means may be used to affix or mount an upper end of piston rod 652 to plate 602, including braising, riveting, welding, gluing and the like. A distal end of each piston rod 652 extends into an associated piston chamber 658 which is formed inside piston tube 660 that extends from plate 604 through plate 606. Typically, an O-ring seal or the like 662 seals the upper end of chamber 658 about rod 652. Disposed on a lower surface of plate 606 is an opening 670 associated with each piston tube 660 which is in fluid communication with the piston chamber 658 disposed within. Openings 670 are configured to be aligned with the center of an upper end 704 of tips 702, as will be described. No nozzles are required as in some prior art systems to couple piston chamber 658 to tips 702.

Plate 602 preferably is coupled to plate 604 only by the plurality of piston rods 652 which extend from plate 602 into piston tubes 660 in plates 604 and 606. Therefore, when plate 602 is raised along with plate 514 within housing 502, piston rods 652 are raised in their respective piston chambers 658, creating a partial vacuum within piston chamber 658 to draw or aspirate liquid into an associated tip 702, as will be described.

As previously described, tray 700 of tips 702 may be inserted and withdrawn from housing 502 independently of head 600. Tray 700 includes an array of openings 706 which are sized to support a comparable array of tips 702. Each tip 702 has an enlarged upper end 704 with a lip 705 which is configured to engage a seal 672 surrounding a corresponding opening 670. The diameter of upper end 704 is greater than that of an opening 706, so that tips 702 are supported on the top surface of tray 700. In one embodiment, each tip 702 tapers to a reduced diameter at distal end 708 through which liquid is drawn from and dispensed into a well 11 in a plate 12. However, tips 702 need not be tapered.

Surrounding each opening 670 is a relatively flexible seal 672 which provides a substantially air and liquid tight seal about lip 705 on upper end 704 to provide an air-tight communication between upper end 704 and opening 670. Typically, seal 672 is a layer of material which covers all of the space between openings 670 on the lower surface of plate 606. A typical material for use in seal 672 is a layer of silicone.

Tray 700 includes side extensions 710 which are configured to rest on surfaces 535 of lower wall 534 of bracket 530, or on clamping surfaces 575. Overlying lips 712 which are spaced from confronting surfaces 535 help hold tray 700 in place. Each surface 535 includes a detent 714 over which an associated extension 710 rides as tray 700 is being inserted into position below head 600. Once tray 700 is in place, detents 714 serve to prevent tray 700 from sliding horizontally out of housing 502 before raising plate 514. A champfer on the back edge of lips 712 precisely positions tray 700 when clamped in place by pushing tray 700 toward the rear wall of housing 502.

Extensions 710 are grabbed by surfaces 535 by raising plate 514 which allows springs 540 to apply an upward force to wall 534 to tightly grab extensions 710, and urge ends 704 against seal 672, and plate 606 against lip 610. In the embodiment of FIGS. 16A and 17A, the tray 700 is positioned by surfaces 577 and detent 581 and extensions 710 are grabbed by surfaces 575 to allow springs 578 to urge ends 704 against seal 672.

In the embodiment of FIG. 16, disposed against the back wall of housing 502 is a stop 716 which limits the distance that tray 700 can be pushed into housing 502 and which is spaced from detents 714 a distance such that when tray 700 is in place on lower wall 534, one end is resting against stop 716, while the other end is in engagement with detents 714, prior to raising plate 514. Preferably, a microswitch 221 is disposed adjacent stop 716 to provide a signal to processor 292 when tray 700 is in place within housing 502.

Tray 700 preferably includes a handle 720 disposed on a forward edge thereof to facilitate grasping, insertion and withdrawal of tray 700.

The operation of pipetting head assembly 500 to insert or withdraw tray 700 will now be described with reference to FIGS. 16 and 16A. If tray 700 is already in place, motor 522 is activated to move belt 528 in a direction which causes plate 514 to move downwardly toward tray 700. As plate 514 moves downwardly, the lower edge thereof engages pegs 546, thereby pushing bracket 530 downwardly toward tray 700 against the upward bias of springs 540. In the embodiment of FIG. 16A, plate 514 engages plates 572. This downward movement of bracket 530 or clamp 574 lowers lower wall 534 or surfaces 575 away from block 510 and tray 700, thereby releasing the clamping pressure on side extensions 710. Once plate 514 is in a position to release tray 700, motor 522 is stopped. At this point, upper ends 704 of tips 702 are spaced from seal 672, and, in FIG. 16, detents 714 are spaced sufficiently far from the underside of lip 712 to allow manual withdrawal of tray 700 by grasping of handle 720. Thereafter, a new tray 700 with clean tips 702 is inserted until the back surface of tray 700 engages stop 716 and triggers microswitch 221 in FIG. 16, or until the back surface of tray 700 engages surfaces 577 in FIG. 16A. At this point, motor 522 is activated to raise plate 514 until plate 514 is raised above pegs 546 in FIG. 16, or above plates 572 in FIG. 16A. Springs 540 or 578 raise wall 534 or clamp 574 so that side extensions 710 are again clamped.

Head 600 is removed or replaced from housing 502 by activating motor 522 until plate 514 is lowered to its lowermost position as indicated by limit switch 560. At this point, plates 602, 604 and 606 are in their closest possible proximity to one another, as any downward movement of plate 606 with respect to block 510 is prevented by slideways 608. All of knobs 630 are unscrewed and shafts 622 are pivoted about associated pins 624 out of cutouts 515. Sufficient space is provided between the back of plate 514 and wall 71 to allow the hand of a user to grasp rear knobs 630 and pivot them out of cutouts 515 toward wall 71. Thereafter, knobs 640 are grasped to withdraw tips 636 from recesses 634 in blocks 633. At this point, head 600 may be grasped and slid manually outwardly along slideways 608. The process is reversed for insertion of a new head 600.

Other optional features of this invention will now be described with particular reference to FIGS. 1, 2, 18, 23 and 24. In one alternative embodiment, this invention includes a fill station 200 which is mounted on one of the plate lifters of plate handling assembly 100, such as plate lifter 103. Fill station 200 may be used in place of mother plates 12 to supply fluid to daughter plates 12. To be so employed, fill station 200 is positioned directly below pipetting head assembly 500 by movement of carriage 106, using X drive motor 126 and Y drive motor 124, as described. Tips 702 are configured to extend into tub 230 of fill station 200 to permit withdrawal of liquid disposed therein. In use, fill station 200 is raised by pad 112 along Z slides 116, a Z drive motor 118 and belt 120. Fill station 200 is disposed in the position shown in FIG. 23. A suitable liquid 220 is supplied to fill station 200 through tube 214 by pump 208 which is controlled by control 210. Tube 214 is coupled to connector 216 which conducts liquid 220 to fill station 200. Liquid 220 is introduced to pump through input tube 212. Fill station 200 is provided with a conventional level detector 218 which makes certain that the level of liquid 220 within fill station 200 is maintained at the desired level so that fill station 200 does not overflow, and so that the distal ends 708 of tips 702 are disposed within liquid 220 below the upper surface thereof. Connector 222 (FIG. 1) for level sensor 218 is disposed on an outer wall of fill station 200.

In another embodiment of this invention, a wash station 250 may be provided. Wash station 250 includes upper chamber 272, lower chamber 274 and cylinders 270. Wash station 250 sits on a pad 112 of one of the plate lifters such as plate lifter 105. In operation, wash station 250 is raised to the position shown in FIG. 24. Wash station 250 is utilized to clean tips 702 which are disposed in tray 700. Pump 254 brings a wash liquid into tube 256 (FIG. 1) and conducts the liquid through tube 258 to a coupling 260 which introduces the wash liquid into wash station 250. Coupling 262 removes used wash liquid from wash station 250 and conducts the used liquid through tube 264 to a waste location. Couplings 260 and 262 may be disconnected if desired, for removal of wash station 250.

Cylinders 270 are in fluid communication with lower chamber 274. In operation, wash liquid comes in through coupling 260 and flows into lower chamber 274 and then into the bottom of cylinders 270. Head 600 is operated to draw wash liquid from chamber 274 and through cylinders 270 into tips 702 to a desired level, and to expel the liquid from tips 702. The expelled liquid is swept up by the continuous flow of fresh liquid into upper chamber 272 which is in fluid communication with coupling 262. Coupling 262 conducts the waste wash liquid through tube 264 where it is sent to a waste collection area. The incoming pressure of liquid produced by pump 254 continually forces liquid from chamber 274 upwardly through cylinders 270 and into chamber 272, so that little or none of the spent liquid used to wash tips 702 is mixed with fresh liquid in chamber 274. Rather, the spent liquid overflows the upper edges of cylinders 270 and is withdrawn. Level sensor 266 maintains the flow of wash liquid at the desired rate by monitoring the level within chamber 272. Level sensor 266 is electrically connected to extend coupling 268.

Preferably, to maintain the cleanliness and integrity of fill tube 214 adjacent connector 216, a protection chamber 276 is provided at one end of wash station 250 into which the distal end of tube 214 projects when work station 250 is raised to tray 700 to be used. Chamber 276 is not in fluid communication with either of chambers 272 or 274. Thus, wash station 250 may be used without disconnecting tube 214 and connector 216 while protecting the tip of tube 214 from any contact with the washing liquid.

In another aspect of this invention, an optional bar code reader 290 may be provided adjacent head assembly 500 on housing wall 71, to read any bar codes placed on plates 12 after plates 12 have been raised by a pad 112 for a pipetting operation. Bar code reader 290 is electronically coupled to processor 292.

Typical methods of operation of this invention will now be described with particular reference to FIGS. 21, 22, and 25–35. It should be noted that the following are exemplary methods of operation of the apparatus of this invention, and that this apparatus may be operated in other ways in accordance with this invention, as will be apparent to one of ordinary skill.

In a typical pipetting operation, as illustrated in FIGS. 25–31, stacker assemblies 20 and 22 contain mother plates 12, while stacker assemblies 24 and 26 contain daughter plates 12. However, it is to be understood that the order could be reversed, so that stacker assemblies 24 and 26 contain the mother plates, while stacker assemblies 20 and 22 contain daughter plates. Typically, mother plates are those which contain a liquid which is to be dispensed into other, empty plates, which are the daughter plates. Also, in a typical operation, stacker assembly 20 contains mother plates whose wells 11 are full of a liquid to be distributed to wells of other plates, while stacker assembly 22 contains used mother plates from which some or substantially all of the liquid has been removed. Similarly, in a typical operation, stacker assembly 24 contains daughter plates into which liquid is to be dispensed from a mother plate, and stacker assembly 26 contains daughter plates whose wells contain a liquid. However, it is to be understood, that the order of the stacker assemblies could be reversed, so that stacker assembly 22 contains filled mother plates, while stacker assembly 20 contains used mother plates, and stacker assembly 26 contains empty daughter plates, while stacker assembly 24 contains filled daughter plates.

Figure 25:
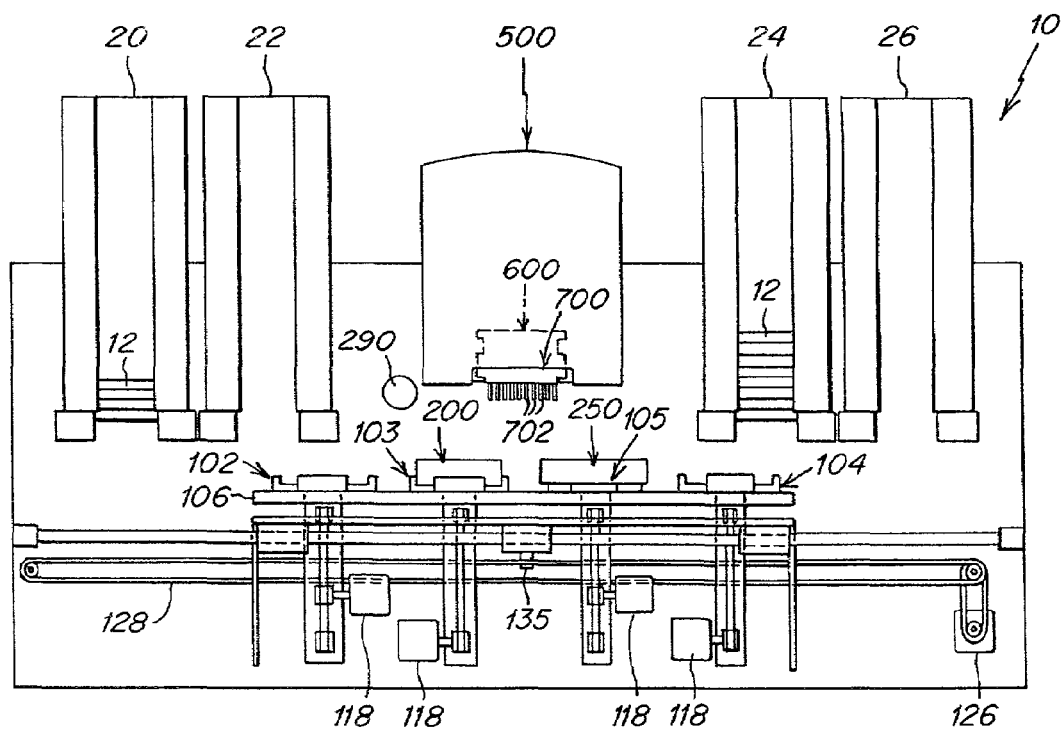
FIG. 25 is a schematic front view of the pipetting system of FIG. 1 illustrating a start position of the system.
Figure 26:
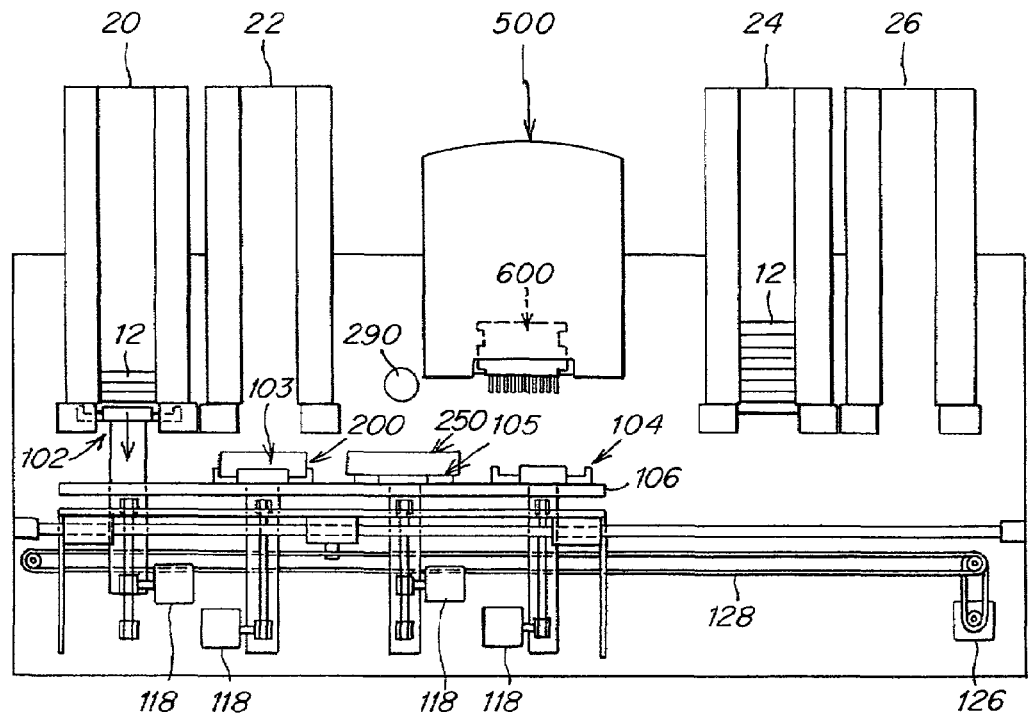
FIG. 26 is a schematic front view of the pipetting system of FIG. 1 illustrating retrieval of a mother plate from a chimney.
Figure 27:
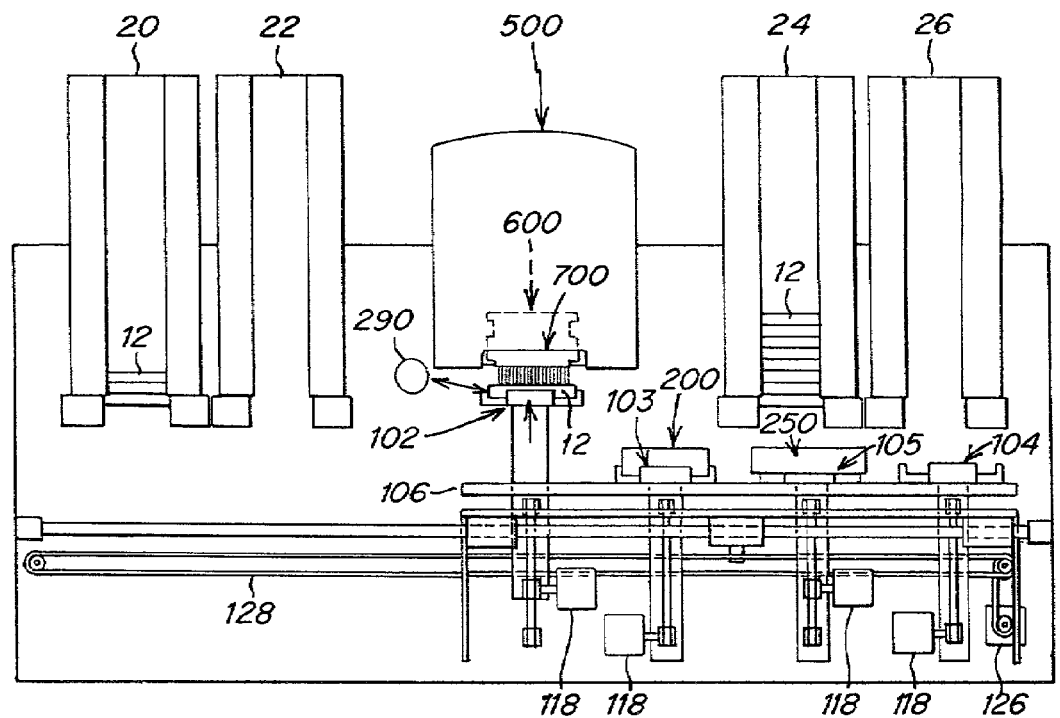
FIG. 27 is a schematic front view of the pipetting system of FIG. 1 illustrating withdrawal of liquid from a mother plate.

FIG. 25 illustrates the condition of the apparatus at the commencement of a pipetting operation in which stacker assembly 20 contains filled mother plates 12, and stacker assembly 24 contains empty daughter plates 12. Typically, carriage 106 is initially centered with respect to housing 14. To initiate the process, as illustrated in FIG. 26, carriage 106 is moved using X drive motor 126 which drives belt 128 to move carriage 106 to the left, as shown in FIG. 26, until pad 112 of plate lifter 102 is disposed below and aligned with stacker assembly 20. The position of pad 112 is adjusted by Y drive motor 206 to be properly aligned. Plate lifter 102 is raised, as previously described, utilizing its associated Z drive motor 118 and belt 120 to retrieve the lowermost mother plate. As plate lifter 102 is raised, pad 112 engages the lower surface of the lowermost mother plate and raises the entire stack of plates 12. If the lowermost plate is stuck to the one above it, Y drive motor 206 may be actuated to oscillate plate lifter 102 back and forth in the Y direction to separate the plates. After the lowermost plate has been lifted to disengage it from arms 85, arms 85 are retracted upon actuation of associated solenoids 84 and 94. Plate lifter 102 is then lowered past retracted arms 85 which are quickly returned to their normal position for engagement of a lip 13 on the next lowermost plate to support the remaining stack of mother plates. Thereafter, as illustrated in FIG. 27, this mother plate is transported using the X drive motor 126 and associated belt 127 until plate lifter 102 is disposed directly beneath head assembly 500. Y drive motor 206 may be used to adjust the Y position of pad 112, if necessary. Plate lifter 102 is then again raised using Z-drive motor 118 and associated belt 120 until distal ends 708 of tips 702 are disposed below the top level of the liquid in associated wells 11 of the mother plate, as shown in FIG. 20. Motor 522 is then activated to raise plate 514 as previously described, through rotation of threaded shafts 560. As plate 514 is raised, plate 602 is raised with respect to plates 604 and 606 a predetermined amount, causing piston rods 652 to rise within associated piston chambers 658. This movement causes a precise amount of liquid to be aspirated into tips 702 through ends 708, as illustrated in FIG. 21. This liquid is then held within tips 702 by retaining plate 514 in a fixed position. If desired, during this process, the bar code on the mother plate may be read by bar code reader 290.

Figure 28:
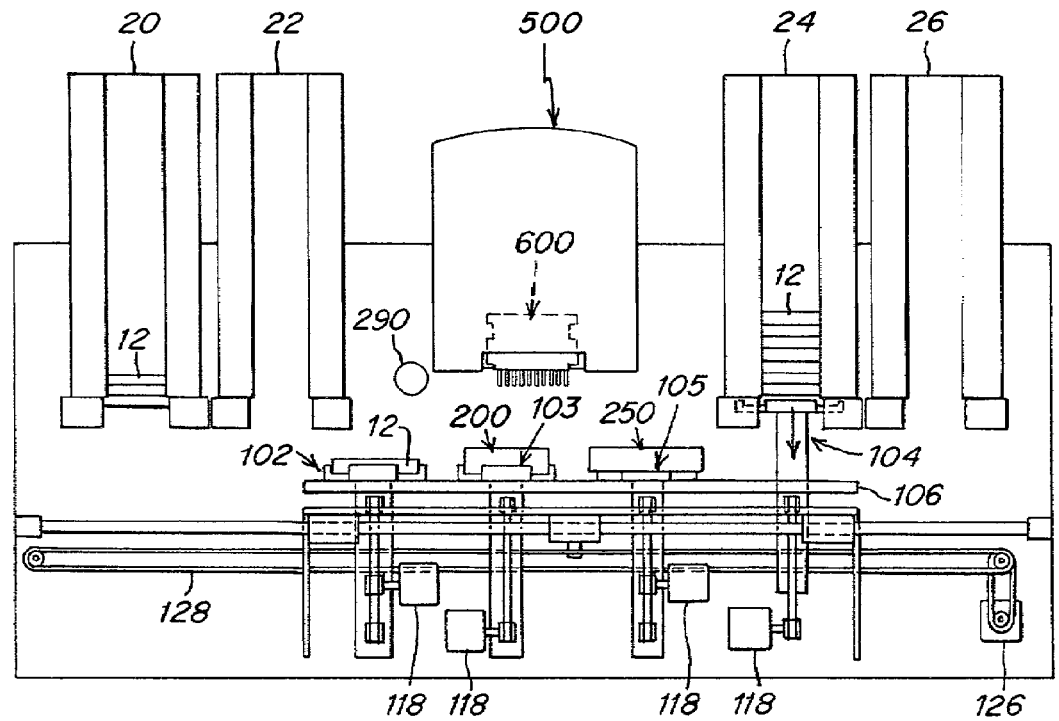
FIG. 28 is a schematic front view of the pipetting system of FIG. 1 illustrating retrieval of a daughter plate from a chimney.
Figure 29:
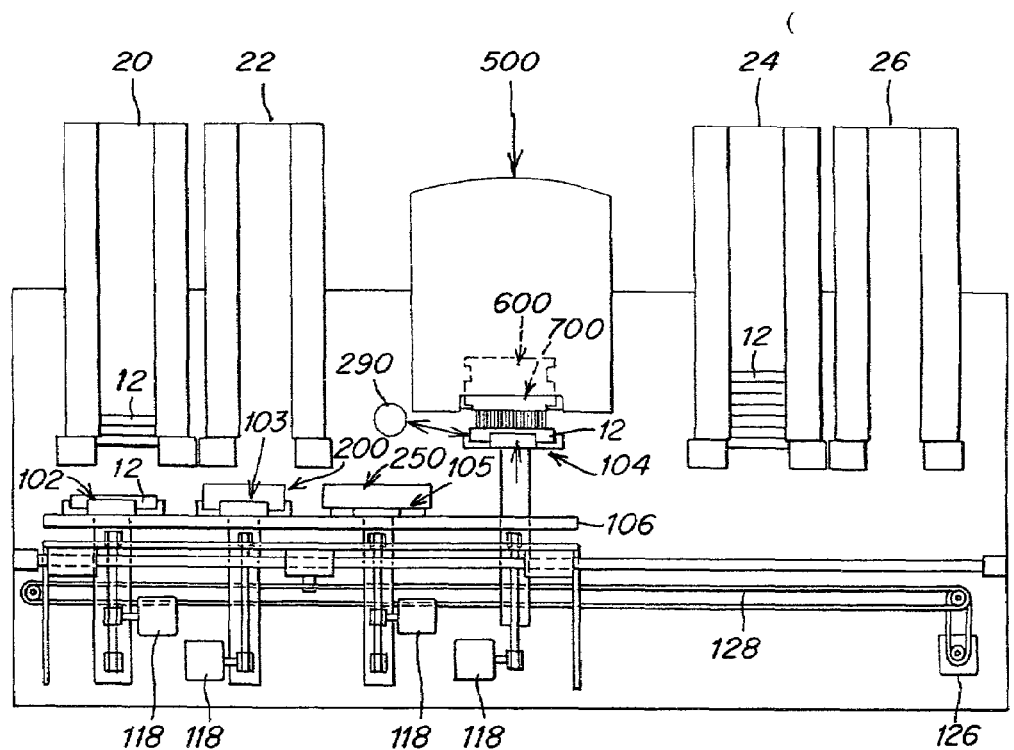
FIG. 29 is a schematic front view of the pipetting system of FIG. 1 illustrating dispensing of liquid into a daughter plate.

Once a precisely determined amount of liquid has been aspirated into tips 702, plate lifter 102 is lowered onto carriage 106. Carriage 106 is then moved in an X direction until second plate lifter 104 is disposed beneath stacker assembly 24, as illustrated in FIG. 28. A lowermost daughter plate is retrieved by pad 112 of plate lifter 104 from stacker assembly 24, in the same manner as previously described with regard to the retrieval of a mother plate from stacker assembly 20. This daughter plate is then transported in the X direction by carriage 106 to head assembly 500, as shown in FIG. 29, where the Y positioning may be adjusted after which it is raised by plate lifter 104 until the ends 708 of each tip 702 are disposed in an associated well 11 which, at this point, contains no liquid. Thereafter, motor 522 is actuated to lower plate 514 a predetermined distance to push piston rods 652 downwardly within piston chambers 658. This precise movement causes a predetermined amount of liquid contained within each tip 702 to be expelled into an associated well 11 disposed in the daughter plate, as illustrated in FIG. 22. Once a desired amount of the liquid has been expelled, Y drive motor 124 and associated belt 126 may be activated to move plate lifter 104 in a Y direction a very small distance to place each end 708 adjacent the edge of associated well 11, as shown in FIG. 22, to swipe any drops disposed on ends 708 of tips 702 into wells 11. Also, during this operation, if desired, a bar code on the side of the daughter plate may be read by bar code reader 290.

Figure 30:
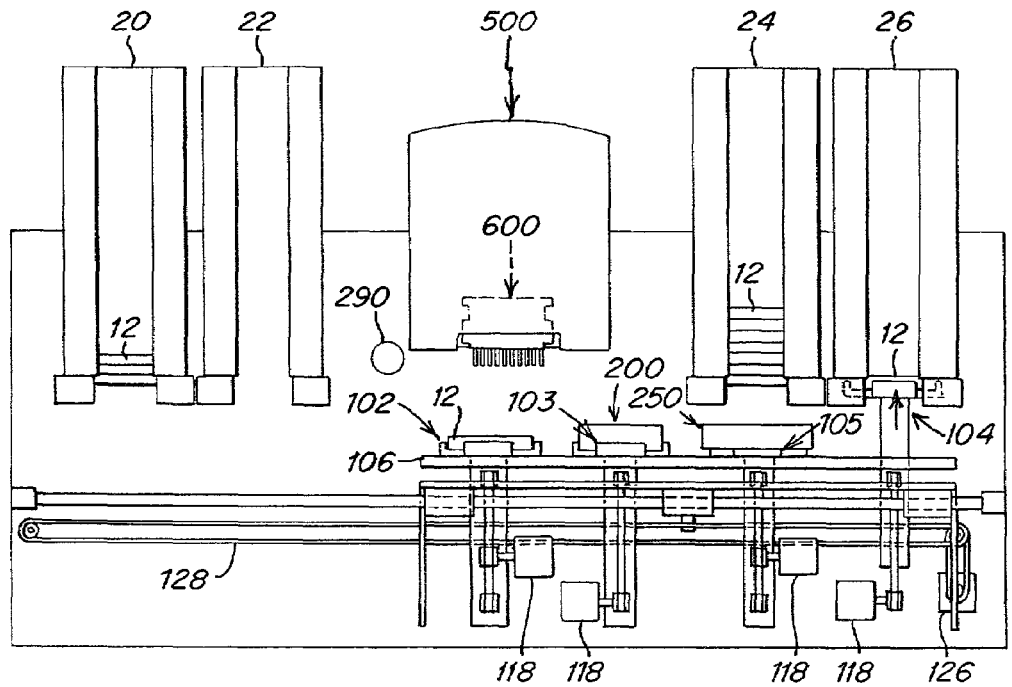
FIG. 30 is a schematic front view of the pipetting system of FIG. 1 illustrating return of a filled daughter plate to a chimney.

Thereafter, the filled daughter plate is returned to stacker assembly 26, as shown in FIG. 30. As the daughter plates are returned, arms 85 are retracted by actuation of solenoid 84. Once lip 13 of the daughter plate is above arms 85, arms 85 return under the bias of spring 86 to their normally extended position in which they engage lip 13 to hold the plate in place in stacker chimney 26, as second plate lifter 104 is withdrawn downwardly.

Figure 31:
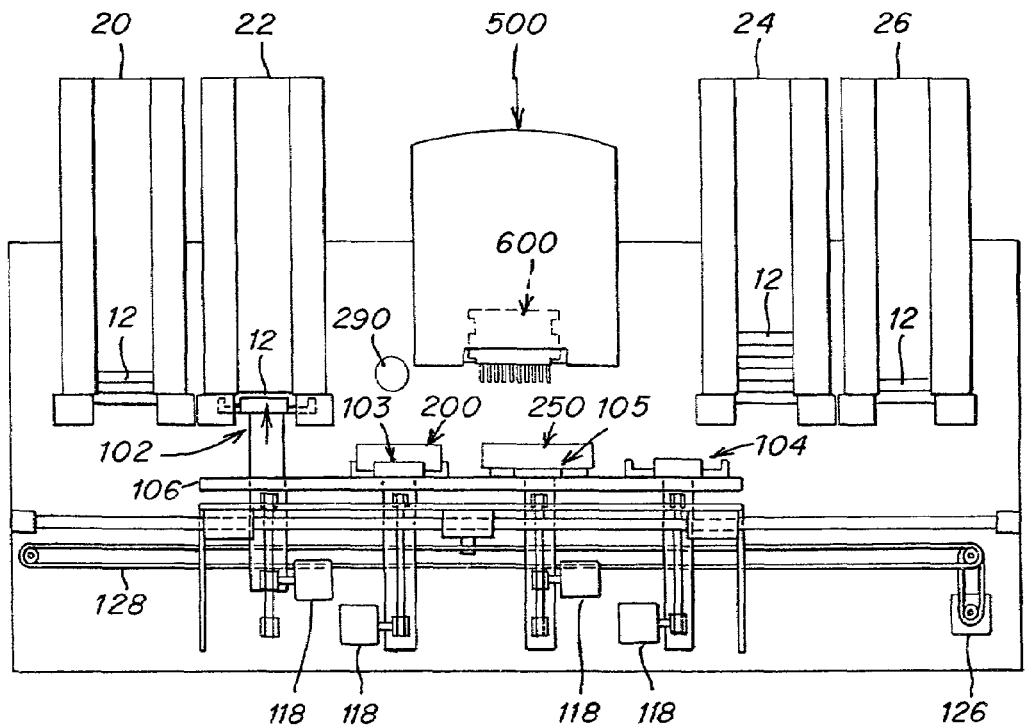
FIG. 31 is a schematic front view of the pipetting system of FIG. 1 illustrating return of an empty mother plate to a chimney.

The foregoing process is repeated until the transfer of liquid in the wells of a mother plate to one or more daughter plates has reached a desired completion point. The used mother plate is placed in stacker assembly 22, as illustrated in FIG. 31 in the same manner as previously described for the placement of the daughter plate in stacker assembly 26. The foregoing process is repeated for a new mother plate containing additional liquid. The process is repeated for additional mother and daughter plates, until the supply of filled mother plates has been exhausted, or until the supply of empty daughter plates has been exhausted, or both.

In many situations, tray 700 includes the same number of tips 702 (and of course, the same number of fluid withdrawal mechanisms 650) as there are wells 11 in both the mother and daughter plates. However, there are instances in which the number of tips 702 is fewer in number than the number of wells 11 in a daughter plate 12 into which liquid is being dispensed. For example, a typical head 600 has an array of 96 or 384 withdrawal mechanisms 650. However, a daughter plate 12 could have as many as 864 or 1536 wells 11. If head 600 had an array of 384 fluid withdrawal mechanisms 650, it could dispense liquid into a daughter plate having 1536 wells 11 in four separate stages, or in four separate quadrants. The daughter plate 12 would be moved by plate handling assembly 100 in X and Y directions to position the daughter plate 12 in the appropriate quadrant with respect to head 600 for dispensing of the predetermined amount of liquid into the wells 11 in that quadrant. This entire process would be controlled by processor 292. In another example, a head 600 having an array of 96 fluid withdrawal mechanisms 650 could service a daughter plate 12 having 864 wells 11 in nine different groupings by appropriate movement of the plate 12 with respect to the head 600 by the plate handling assembly 100. Similarly, liquid could be extracted from the wells of a mother plate in different quadrants or groupings for dispensing into daughter plates by manipulation of the mother plate with respect to head 600 using plate handling assembly 100.

Thereafter, the empty chimney 28 from stacker assembly 20 may be withdrawn and replaced with a chimney full of mother plates. In addition, chimney 28 from stacker assembly 22 containing spent mother plates is withdrawn and replaced with an empty chimney 28. Additionally, chimney 28 of stacker assembly 24 which has been emptied of daughter plates can be replaced with a chimney 28 containing clean daughter plates. Finally, chimney 28 of stacker assembly 26 containing filled daughter plates can be removed and replaced with an empty chimney.

In each instance, the chimney 28 is raised upwardly by handle 60 so that button 66 slides out of slot 67, and so that button 68 slides out of slot 64. In each instance, the lowermost plate is supported on lips 13 by arms 85 as the assembly is being raised. The plates are slowly dropping within the chimney as the chimney is being raised. At the same time, flaps 74 are pivoting to their open position under the influence of spring 78 as flaps 74 ride up and over associated upstanding walls 91. At just about the time that flaps 74 are in their open position and engaging the lower surface of the lowermost plate 12, the chimney is raised sufficiently so that the lowermost plate is out of engagement with arms 85 of solenoids 84 and 94. Arms 85 slide downwardly out of the chimney. Arms 85 on solenoids 84 ride downwardly and out through slots 80. At this point, the plates 12 are supported by flaps 74, and the chimney may be carried to any location desired. If it is desired to remove plates 12 from a chimney, doors 40 may be opened by raising each door until pin 52 is out of registration with associated hole 54 and thereafter by pivoting each door 40 about associated hinge 38. At this point, the individual plates may be manually retrieved from the chimney. For empty chimneys, the doors 40 may be opened in the same manner and fresh filled mother plates, or empty daughter plates may be placed in the chimney. Thereafter, the doors 40 are closed by pivoting each door 40 about associated hinge 38 from its open position to its closed position at which time associated pins 52 automatically fall into associated holes 54 under the influence of gravity when pin 52 and hole 54 are in registration with one another, causing each door 40 to fall downwardly to lock the door into position to prevent the plates from falling out while the chimney is being transported.

Figure 32:
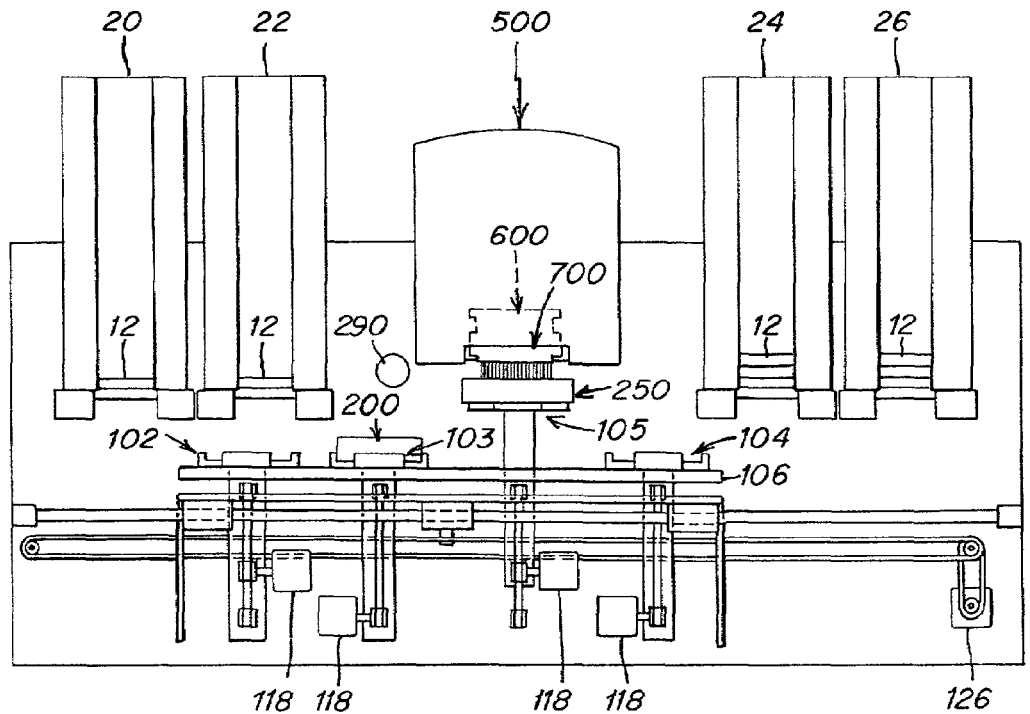
FIG. 32 is a schematic front view of the pipetting system of FIG. 1 illustrating use of the wash station.

Wash station 250 may be used to wash tips 702 between operations by raising station 250 to the position shown in FIG. 32 and performing a wash operation as previously described with respect to FIG. 24, by aspirating a wash liquid into tips 702 from associated cylinders 270, and by expelling the wash liquid from the tips 702, as shown in FIG. 24. As previously discussed, this aspiration process is accomplished by raising and lowering plate 514.

Figure 33:
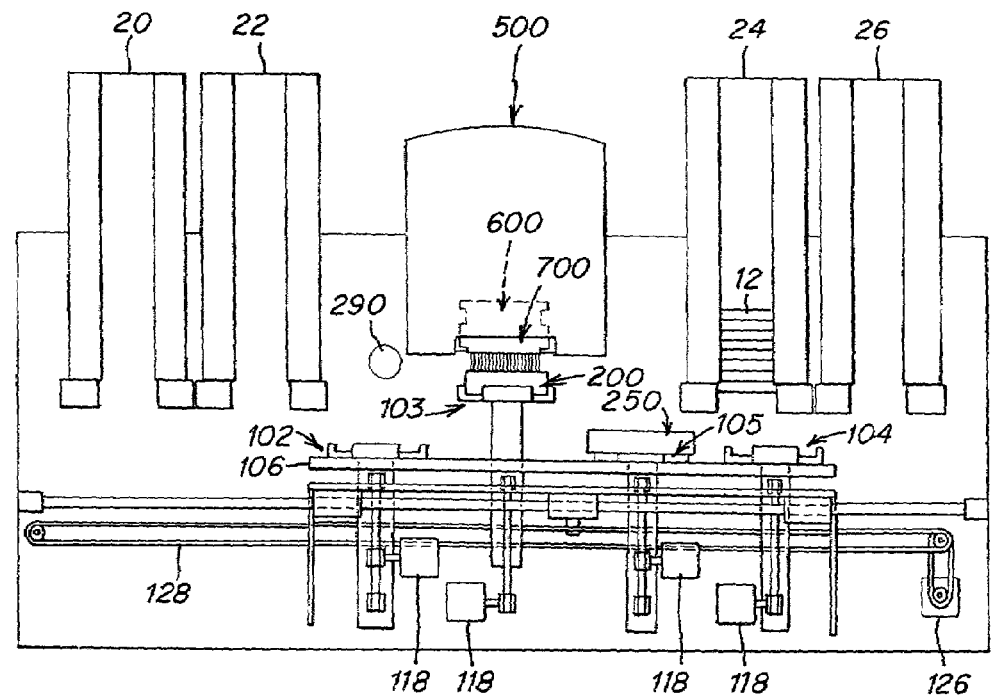
FIG. 33 is a schematic front view of the pipetting system of FIG. 1 illustrating withdrawal of fluid from the fill station.
Figure 34:
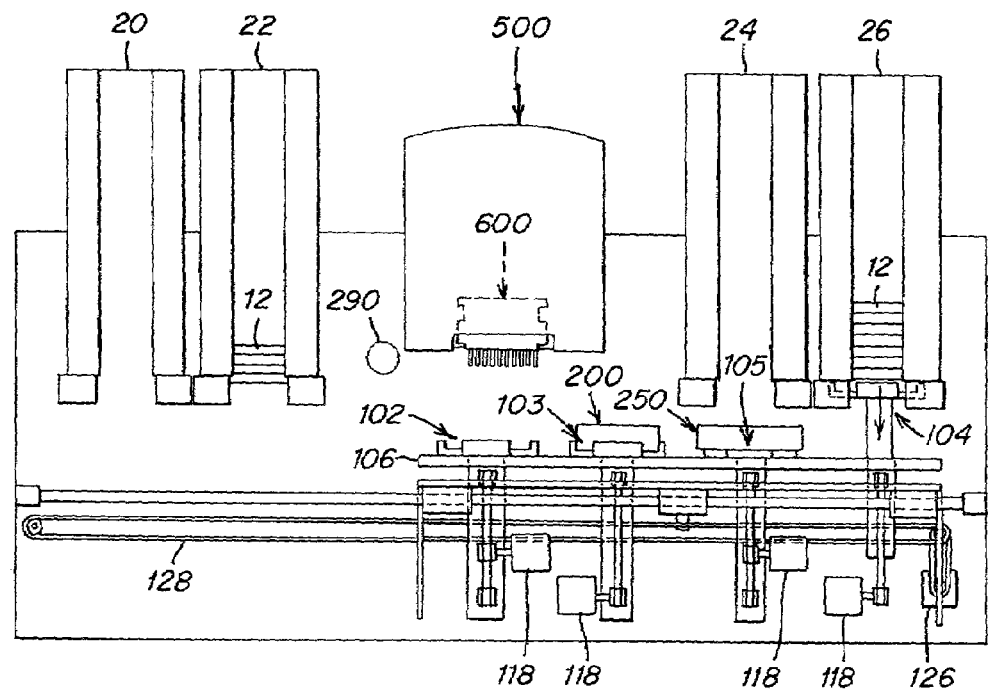
FIG. 34 is a schematic front view of the pipetting system of FIG. 1 illustrating withdrawal of an empty daughter plate to be filled with liquid from the fill station.
Figure 35:
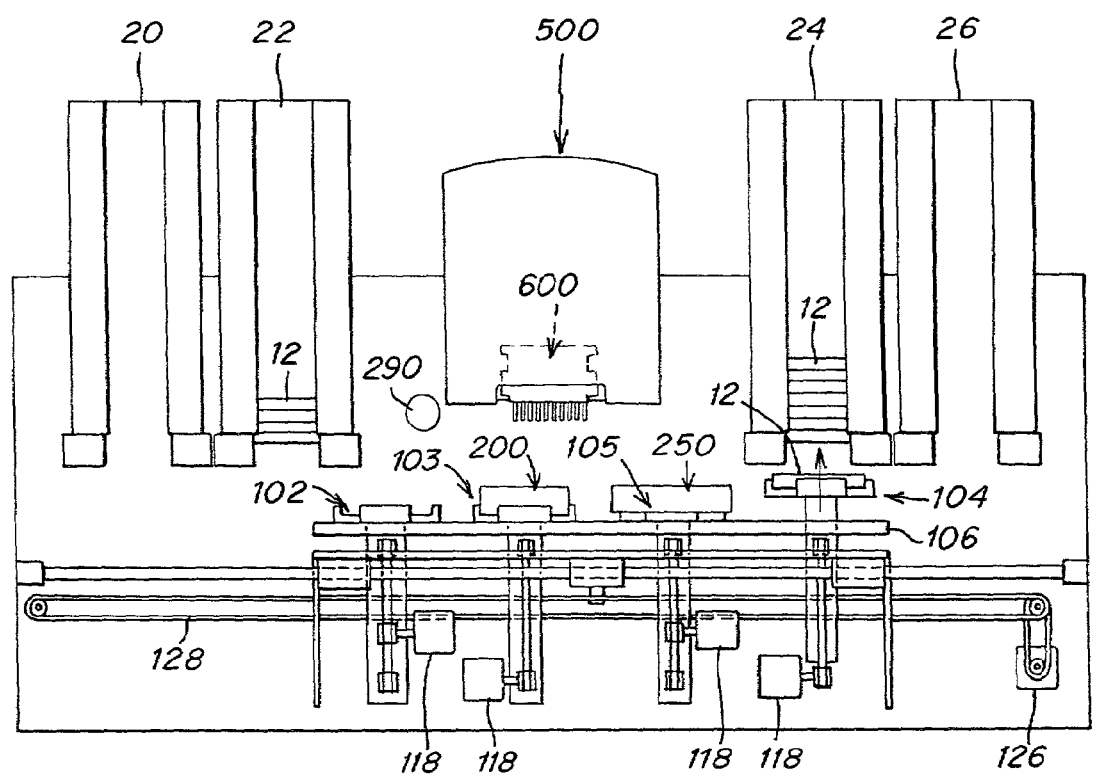
FIG. 35 is a schematic front view of the pipetting system of FIG. 1 illustrating return of a daughter plate after being filled with fill station liquid from the pipetting head.

Instead of using mother plates as previously discussed with respect to FIGS. 25–31, fill station 200 may be employed. The method of operation of this aspect of the invention will now be described with particular reference to FIGS. 33–35. In the first step, as illustrated in FIG. 33, carriage 106 is moved until plate lifter 103 is disposed beneath head assembly 500. Plate lifter 103 is then raised in the manner previously described until fill station 200 is disposed in the position shown in FIG. 33, in which the ends 708 of tips 702 are each disposed below the surface of liquid 220 within tub 230. Tub 230 is kept in a filled condition by pump 208 which pumps the desired liquid from input tube 212 through tube 214 and connector 216 and into tub 230. Level detector 218 maintains liquid 220 at the desired level by controlling actuation of pump 208 in a known manner. A predetermined amount of liquid 220 is aspirated into tips 702 in the manner previously described, by raising plate 514. Thereafter, plate lifter 103 is lowered onto carriage 106 is moved in the X direction to the position as shown in FIG. 34 in which second plate lifter 104 is utilized to retrieve an empty daughter plate from either stacker assembly 24 or stacker assembly 26. Thereafter, the empty plate is transported by carriage 106 to head assembly 500 where plate lifter 104 raises the plate so that ends 708 of tips 702 are positioned within wells 11. Thereafter, the aspirated liquid in tips 702 is expelled into the wells 11 of the plate 12 in the manner previously described. Second plate lifter 104 is then moved by carriage 106 in the X direction until plate lifter 104 is in the position shown in FIG. 35 disposed below stacker assembly 24. Second plate lifter 104 is then raised to deposit the filled daughter plate in stacker assembly 24 in the manner previously described. It should be understood, of course, that the empty daughter plates may be retrieved from any one of the stacker assemblies 20–26, and replaced in any other ones of the stacker assemblies 20–26 when using fill station 200. Thereafter, the foregoing process is repeated, until all of the empty daughter plates have been filled with a desired liquid from the fill station 200.

It is to be understood that the foregoing methods of operation of system 10 of this invention are intended to be exemplary of the manner in which system 10 may be operated, and are not intended to be limiting. System 10 may be operated in any other manner desired by the user which achieves the required pipetting functions. The location of the stacker assemblies containing mother and daughter plates may be modified or shifted in any way selected by the user. The processor 292 may be programmed by one of ordinary skill to operate system 10 utilizing any configuration desired by the user. Furthermore, neither fill station 200 nor wash station 250 need be utilized. Plate lifters 103 and 105 may be utilized for purposes other than a fill station 200 or a wash station 250. A single plate lifter may be utilized to perform all of the functions of system 10. Finally, the number of stacker assemblies used may be two, four, six or even more depending upon the needs of the user. These changes may be accommodated by making obvious programming changes to processor 292.

It is also to be understood that plates 12 of different sizes having different numbers of wells 11 may be utilized. In addition, plates 12 of different thicknesses, or having wells 11 of different depths may be used also. Since head 600 and tray 700 are replaceable, a tray 700 may be selected that is compatible with head 600, and head 600 and tray 700 may be selected to be compatible with the number, size and spacing of the wells 11 in plates 12. Appropriate programming changes to processor 292 may be made to accommodate wells of different capacities so that greater or lesser amounts of liquid may be drawn into tips 702 and expelled into daughter plates.

Modifications and improvements will occur within the scope of this invention to those skilled in the art. The above description is intended to be exemplary only. The scope of this invention is defined only by the following claims and their equivalents.

What is claimed is:

1. A liquid dispenser comprising:
   a housing;
   a dispensing head comprising a plurality of chambers and associated pistons for withdrawing a measured amount of a liquid from a source and expelling another measured amount of the liquid in a first direction from said plurality of chambers and into the wells of a plate;
   apparatus for moving each piston within its associated chamber; and
   slideways disposed on the housing for supporting the dispensing head and extending in a second direction generally perpendicular to the first direction, said dispensing head being unattached to the slideways to allow said dispensing head to be slidable into and out of the housing along the slideways in said second direction.

2. The liquid dispenser as recited in claim 1 further comprising manually operable apparatus attached to the dispensing head for attaching the dispensing head to the housing at a point spaced vertically above the slideways.

3. The liquid dispenser as recited in claim 2, wherein the apparatus for attaching the dispensing head comprises:
   a plurality of threaded shafts mounted to the dispensing head;
   a plate disposed within the housing;
   cutouts on the plate for receiving the threaded shafts; and
   a knob threadably mounted on each threaded shaft, said knobs being rotatable about the shaft to be screwed into engagement with said plate for securing said dispensing head to the plate.

4. The liquid dispenser as recited in claim 1 further comprising:
   a plurality of tips, each tip being associated with one of the chambers, each tip having a first end with an enlarged opening, and a second end having a smaller opening than the opening of the first end, the first end of each tip being in fluid communication with an opening of an associated chamber; and
   a flexible seal extending around each chamber opening and being engaged by the first ends of the tips to provide a substantially air and liquid-tight seal between the first ends of the tips, and the associated openings of the chambers.

5. The liquid dispenser as recited in claim 4, wherein the seal comprises a layer which covers substantially all space between adjacent openings of the chambers.

6. The liquid dispenser as recited in claim 4, wherein the seal is formed of silicone.

7. The liquid dispenser as recited in claim 4 wherein the tips are carried in a tray, the liquid dispenser further comprising:
   a clamp for clamping the tray against a wall of the housing; and
   apparatus urging the clamp against the wall of the housing for maintaining a clamping force on the tray against the housing wall.

8. The liquid dispenser as recited in claim 7, wherein the urging apparatus comprises at least one spring.

9. The liquid dispenser as recited in claim 7, wherein the clamp is engageable by the apparatus for moving each piston within its associated chamber to move the clamp away from the wall of the housing against the clamping force of the urging apparatus to release the clamping force on the tray.

10. The liquid dispenser as recited in claim 1 wherein said apparatus for moving each piston within its associated chamber comprises:
    a plate coupled to each of said pistons; and
    a motor operably coupled to the plate for moving the plate toward and away from the chambers to cause movement of said pistons within the chambers.

11. The liquid dispenser as recited in claim 10 further comprising:
    a tray containing a plurality of tips, each tip including a first end having an enlarged opening and a second end having an opening smaller than the opening of the first end;
    at least one bracket being mounted on the housing and being movable with respect to the housing for clamping the tray against the housing so that the first end of each tip is in fluid communication with one of said chambers; and
    a connection between the plate and the bracket for moving the bracket away from the housing in response to movement of the plate to release the tray.

12. The liquid dispenser as recited in claim 11 further comprising a spring for urging the at least one bracket against the housing for providing a clamping force on the tray.

13. The liquid dispenser as recited in claim 3, wherein said housing plate is coupled to said apparatus for moving each piston.

14. The liquid dispenser as recited in claim 13, wherein said threaded shafts are connected to said pistons in said dispensing head and wherein said apparatus for moving each piston is coupled to the pistons through said threaded shafts.

15. A liquid dispenser comprising:
- a housing;
- a dispensing head comprising a plurality of chambers and associated pistons for withdrawing a measured amount of liquid from a source and expelling another measured amount of the liquid into the wells of a plate;
- apparatus for moving each piston within its associated chamber;
- slideways disposed on said housing for supporting said dispensing head, said dispensing head being slidable into and out of said housing along said slideways; and
- manually operable apparatus attached to said dispensing head for retaining said dispensing head within said housing, said apparatus for retaining the dispensing head comprising:
  - a plurality of threaded shafts mounted to said dispensing head;
  - a plate disposed within said housing;
  - cutouts on said plate for receiving said threaded shafts; and
  - a knob threadably mounted on each shaft, said knobs being rotatable about said shafts to be screwed into engagement with said plate for securing said dispensing head to said plate.

16. The liquid dispenser as recited in claim 15, wherein said housing plate is coupled to said apparatus for moving each piston.

17. The liquid dispenser as recited in claim 16, wherein said threaded shafts are connected to said pistons in said dispensing head and wherein said apparatus for moving each piston is coupled to said pistons through said threaded shafts.

* * * * *